(12) United States Patent
Shahaf et al.

(10) Patent No.: US 9,826,914 B2
(45) Date of Patent: *Nov. 28, 2017

(54) FUNCTIONAL ANALYSIS OF NEUROPHYSIOLOGICAL DATA

(71) Applicant: Elminda Ltd., Herzlia (IL)

(72) Inventors: Goded Shahaf, Haifa (IL); Amir B. Geva, Tel-Aviv (IL); Tomer Carmeli, Kiryat-Tivon (IL); Noga Pinchuk, Zikhron-Yaakov (IL); Israel Tauber, RaAnana (IL); Amit Reches, Binyamina (IL); Guy Ben-Bassat, Kibbutz Beit Zera (IL); Ayelet Kanter, Yokneam Ilit (IL); Urit Gordon, Kiryat-Tivon (IL)

(73) Assignee: Elminda Ltd., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,933

(22) Filed: Apr. 17, 2014

(65) Prior Publication Data

US 2014/0228702 A1 Aug. 14, 2014

Related U.S. Application Data

(63) Continuation of application No. 12/745,560, filed as application No. PCT/IL2008/001558 on Nov. 30, 2008, now Pat. No. 8,706,205.

(60) Provisional application No. 60/990,930, filed on Nov. 29, 2007.

(51) Int. Cl.
| | |
|---|---|
| *A61B 5/04* | (2006.01) |
| *A61B 5/0476* | (2006.01) |
| *A61B 5/0482* | (2006.01) |
| *A61B 5/00* | (2006.01) |

(52) U.S. Cl.
CPC ...... *A61B 5/04012* (2013.01); *A61B 5/04009* (2013.01); *A61B 5/0476* (2013.01); *A61B 5/0482* (2013.01); *A61B 5/726* (2013.01); *A61B 5/742* (2013.01); *A61B 5/7203* (2013.01)

(58) Field of Classification Search
None
See application file for complete search history.

(56) References Cited

U.S. PATENT DOCUMENTS

| | | | |
|---|---|---|---|
| 5,083,571 | A | 1/1992 | Prichep |
| 5,299,118 | A | 3/1994 | Martens et al. |
| 6,937,961 | B2 | 8/2005 | Cabral et al. |
| 8,706,205 | B2 | 4/2014 | Shahaf et al. |
| 2002/0099280 | A1 | 7/2002 | Huang |
| 2005/0059874 | A1 | 3/2005 | Fuchs et al. |

(Continued)

FOREIGN PATENT DOCUMENTS

| | | |
|---|---|---|
| WO | WO 2007/138579 | 12/2007 |
| WO | WO 2009/069134 | 6/2009 |

OTHER PUBLICATIONS

Requisition by the Examiner and the Examination Search Report dated Apr. 29, 2015 from the Canadian Intellectual Property Office Re. Application No. 2,706,640.

(Continued)

*Primary Examiner* — Etsub Berhanu

(57) ABSTRACT

A method for functional analysis of neurophysiological data by decomposing neurophysiological data and EEG signal to form a plurality of signal features. The signal features may then optionally be analyzed to determined one or more patterns.

16 Claims, 21 Drawing Sheets

(56) References Cited

U.S. PATENT DOCUMENTS

| | | |
|---|---|---|
| 2005/0177058 A1 | 8/2005 | Sobell |
| 2006/0111644 A1 | 5/2006 | Guttag et al. |
| 2006/0126944 A1 | 6/2006 | Loui et al. |
| 2006/0149160 A1 | 7/2006 | Kofol et al. |
| 2007/0100251 A1 | 5/2007 | Prichep |
| 2008/0249430 A1 | 10/2008 | John et al. |
| 2011/0004115 A1 | 1/2011 | Shahaf et al. |

OTHER PUBLICATIONS

Translation dated May 18, 2015 of Office Action dated Apr. 28, 2015 from the Israel Patent Office Re. Application No. 235394.
Office Action dated Apr. 28, 2015 from the Israel Patent Office Re. Application No. 235394.
International Preliminary Report on Patentability dated Jun. 10, 2010 from the International Bureau of WIPO Re. Application No. PCT/IL2008/001558.
International Search Report and the Written Opinion dated Apr. 7, 2009 from the International Searching Authority Re.: Application No. PCT/IL08/01558.
Notice of Allowance dated Dec. 9, 2013 from the US Patent and Trademark Office Re. U.S. Appl. No. 12/745,560.
Office Action dated 03 dated 2012 from the Israel Patent Office Re. Application No. 206005 and Its Translation Into English.
Office Action dated Oct. 3, 2013 from the Israel Patent Office Re. Application No. 206005 and Its Translation Into English.
Official Action dated Dec. 5, 2012 from the US Patent and Trademark Office Re. U.S. Appl. No. 12/745,560.
Official Action dated Aug. 14, 2013 from the US Patent and Trademark Office Re. U.S. Appl. No. 12/745,560.
Supplemental Notice of Allowability dated Mar. 3, 2014 from the US Patent and Trademark Office Re. U.S. Appl. No. 12/745,560.
Supplementary European Search Report and the European Search Opinion dated Sep. 14, 2015 from the European Patent Office Re. Application No. 08854552.0.
Requisition by the Examiner dated Apr. 28, 2016 from the Canadian Intellectual Property Office Re. Application No. 2,706,640.
Requisition by the Examiner dated Mar. 10, 2017 from the Canadian Intellectual Property Office Re. Application No. 2,706,640.

| (SUBJECT#, EPOCH #, STIMULUS) | (1.1.Lt) | (1.1.Rt) | (1.1.Lt) | (1.1.Lt) | (1.1.Lt) | (1.1.Lt) | (1.1.Rt) | (1.1.Rt) | (1.1.Rt) | (1.1.Rt) |
|---|---|---|---|---|---|---|---|---|---|---|
| FREQUENCY BAND (Hz) | [7,12] | [7,12] | [7,12] | [7,12] | [7,12] | [7,12] | [7,12] | [7,12] | [7,12] | [7,12] |
| TIME(MS) | 12 | 40 | 40 | 132 | 140 | 140 | 364 | 364 | 364 | 364 |
| ELEC # | E7 | E29 | E30 | E29 | E27 | E28 | E25 | E50 | E52 | E53 |
| AMP | ++ | -- | -- | -- | -- | -- | ++ | ++ | ++ | ++ |

FIG.5C

FUNCTIONAL ANALYSIS OF NEUROPHYSIOLOGICAL DATA

RELATED APPLICATIONS

This application is a continuation of U.S. patent application Ser. No. 12/745,560 filed on Sep. 20, 2010, which is a National Phase of PCT Patent Application No. PCT/IL2008/001558 having International filing date of Nov. 30, 2008, which claims the benefit of priority of U.S. Provisional Patent Application No. 60/990,930 filed on Nov. 29, 2007. The contents of the above Applications are all incorporated herein by reference.

FIELD OF THE INVENTION

The present invention relates to methods of functional analysis of neurophysiological data and, more particularly, to methods for detecting one or more patterns in such data.

BACKGROUND OF THE INVENTION

Neurophysiological data includes any type of signals obtained from the brain. Such signals may be measured through such tools as EEG (electroencephalogram), which is produced using electroencephalography. Electroencephalography is the neurophysiologic measurement of the electrical activity of the brain (actually voltage differences between different parts of the brain), performed by recording from electrodes placed on the scalp or sometimes in or on brain tissue. As used herein, the term "neurophysiological data" also refers to brain imaging tools, including but not limited to CAT (computer-aided tomography) scans (otherwise known as CT or computed tomography) scans, PET (positron emission tomography) scans, magnetic resonance imaging (MRI) and functional magnetic resonance imaging (fMRI), ultrasound and single photon emission computed tomography (SPECT).

Although such data is extremely valuable, to date analysis of the data has suffered from lack of suitable automatic tools. Although various analytical tools are available, they require extensive human interaction and are also prone to artifacts.

SUMMARY OF THE INVENTION

The background art does not teach or suggest a method for analyzing neurophysiological data which is highly automated. The background art also does not teach or suggest such a method which decomposes the data to a plurality of signal features, which may then be analyzed to determine one or more patterns.

The present invention overcomes these drawbacks of the background art by providing a method for decomposing neurophysiological data to form a plurality of signal features. The signal features may then optionally be analyzed to determine one or more patterns. The patterns themselves may optionally be combined to form more comprehensive patterns. Searches may optionally be performed through a plurality of different patterns in order to determine which patterns may be combined, for example.

According to some embodiments of the present invention, the neurophysiological data comprises EEG data. The EEG data is preferably decomposed to form a plurality of signal features. Such signal features preferably represent important features of the data. Signal feature definition is preferably provided for each response to a stimulus. The resultant patterns determined from signal feature analysis may optionally be source localization patterns, or alternatively may optionally be patterns of the signal features themselves, or a combination thereof.

Optionally and more preferably, the EEG data is collected at least before and after the subject has performed a task and/or action (also conceptual task/action), which then forms the stimulus or stimuli for signal feature definition. Typically an on-going EEG is used, such that data is collected continuously before, during and after performance of the task and/or action. Signal features are then preferably used to indicate or mark any difference(s) in the EEG signal(s) before, during and after performance (see for example FIG. 1).

Various types of tasks may optionally be used, including but not limited to an on-going task/action, such as watching a movie for example. A single task and/or action may optionally be used, such as providing an audible signal to the user, such as a simple sound. The sound may optionally be played once or may be played repeatedly (it may also be on-going). For a repeated sound, the subject will eventually be conditioned and will pay less attention (a process known as habituation), but there still will be a response from the brain. All of these different aspects of task and/or action performance, including habituation, may optionally and preferably be used for the determination and indication of signal features.

The previous example of providing an audible sound relates to a lower-level cognitive task. A higher level cognitive task may also optionally be performed, in which case the brain of the subject focuses on such a higher level task. Although other brain activities still occur, the degree of focus also increases the ease of determining signal features for the different EEG signal(s) measured during such a task, as a large portion of the EEG signals are related to the higher level cognitive task. A non limiting example of a higher level cognitive task is one in which the subject is requested to push a button if a high pitch sound is heard; if a low pitch sound is heard then the subject is not to push the button. These types of stimuli are used during surgery, even with an unconscious/sedated patient.

More preferably, the stimuli are structured so as to provide the maximum possibility of signal feature definition. Repetitions increase the ease of signal feature definition because it becomes easier to locate true signal(s) due to the stimuli. However, as a task and/or action is repeated, the subject will react to varying degrees for subsequent repetitions. Multiple trials are preferred for simple stimuli, but may be less suitable for more complicated tests; however this could easily be determined by one of ordinary skill in the art. In addition, measurement of spontaneous brain activity may also optionally be performed, additionally or alternatively to measuring brain activity during one or more specific tasks and/or actions.

The EEG data is optionally and preferably first filtered according to one or more filters. However, optionally no filters are use to eliminate noise, as no anti-noise filters are required. Non-limiting examples of filters which may optionally be used include bandpass filter, bandwidth filter and the like.

A bandwidth filter, as its name suggest, permits only a certain range of frequencies to pass. Such filters may optionally and preferably be used in order to isolate important signal(s). Optionally particular bandwidth filter(s) may be selected in advance according to the desired type of data to be collected. For example some bandwidths are known to be related to cognitive tasks. Delta waves are known to be associated with sleep, while alpha waves are associated with relaxation. Other non-limiting examples of known types of waves for which particular bandwidth filters may be selected include mu, beta, gamma, and theta waves. The selection of a particular bandwidth filter forms part of the description of a signal feature and may be quite useful for signal feature definitions, as they assist to remove signals from non-related tasks or activities, and to focus on specific thought actions in the brain. Other types of filters may also optionally be used in a similar manner.

Another type of "filter" is the practice of averaging EEG data from multiple trials of a single subject to look for significant signals and/or patterns. Averaging however is a type of lowpass filter. According to some embodiments of the present invention, EEG data from a single trial of a single subject is used for pattern construction as described herein such that averaging from multiple trials is not used, in which case another type of filter or filters may optionally be selected.

Optionally, the data may be processed to remove noise. Such noise may optionally be removed through the use of heuristic filters or other processing, to remove expected interference with the desired signals. Also, processing for noise may optionally be "tuned" for a particular subject.

A filter (or a combination thereof) may optionally be used as a template for expected results and/or an expected diagnosis, such that the filter(s) may be a type of signal feature. A non-limiting example of such a filter, in addition to the above described types of filters, is to provide a template such as an expected sinus form for example.

Signal features may also optionally and preferably be defined after filtering, for example by assignment of signal features through the location of peaks. The use of filters enables particular peaks to be more easily identified. Peaks may optionally be identified according to their height and frequency for example. Peak assignment may also optionally be used even if no stimulus has been provided; however, in this case, preferably such an assignment is performed in comparison to a predetermined pattern, in order (for example) to more easily remove noise and/or to identify signal features within other brain activities. Additionally or alternatively, according to some embodiments, optionally signal features are assigned to non-peak waveforms with biologically relevant shapes and/or temporal properties.

Optionally and preferably, the decomposition to signal features includes the determination of timing (latency), amplitude and frequency for each peak.

A non-limiting example of decomposition to signal features comprises the use of clustering to locate one or more important features. Clustering is preferably performed after the above filtering process; the identity of the filter preferably forms part of the clustering, such that data having at least similar peaks and/or other identifiable features after filtering may be clustered.

Optionally and more preferably, a cluster is identified which has a sufficiently large number of peaks at the same time, frequency and amplitude, thereby defining the same event in many electrodes and/or patients. The number of peaks required is preferably determined according to a statistical threshold or cut-off. The permitted variance within the cluster is preferably determined according to the size of a sliding window; the greater size of the window, the greater variance permitted for the cluster. The permitted variance is optionally a fixed parameter and/or a flexible variable. Also optionally clusters are compared according to an amount of permitted variance between clusters.

A collection of clusters may optionally form an activity network, as described in greater detail with regard to FIG. 13. Once the data have been analyzed to form clusters, such clusters are preferably used to search through existing patterns. However, it should be noted that optionally the signal features themselves are used to search for patterns, without necessarily relying on first clustering the signal features. Preferably, an exhaustive search of all patterns is performed even though such a search is NP hard. To assist in more rapid searching, optionally one or more heuristics may be used, for example in terms of expected clusters and/or other features of the data, and/or by applying one or more templates for example. Hierarchical clustering may also optionally be used. The activity network, as well as pattern analysis, also provides greater sensitivity and specificity for comparing groups of subjects.

Patterns are preferably also analyzed to determine whether a plurality of such patterns should be combined, such that for example the combination "pattern A and B" could itself form a new pattern. A combination of patterns may optionally also include the absence of a particular pattern; for example the combination "pattern A but not C" relates to the presence of pattern A but the absence of pattern C.

The significance of the combination is more preferably determined according to one or more statistical analyses. As described in greater detail below, one or more statistical tests are preferably performed, to determine whether such a combination should be accepted.

According to some embodiments of the present invention, the localization of a particular signal within the brain is preferably determined through analysis of the obtained pattern(s) or alternatively through analysis of the clusters themselves. The problem of localization, or spatial resolution, of the electrode signals cannot be solved by adding more electrodes as they will be mutually dependent. One non-limiting example of a method for such localization features the use of low resolution electromagnetic tomography (LORETA), as described for example in PCT Application NO. PCT/IL2007/000639. LORETA provides a true three dimensional localization of the EEG signals. However, LORETA does not always present a completely correct solution, as the location may be incorrectly determined and/or the resolution may be insufficient to detect an area shift.

Surprisingly, the present inventors have found that an incorrect location for EEG data may be overcome by determining the likelihood for each potential solution to the problem of localization. The likelihood of a particular location being the correct source localization for an EEG signal may optionally and preferably be based on electrophysiological information.

Functional information may also optionally be used for localization, by determining which area of the brain is likely to be involved in generating a particular signal. Such functional information may also optionally include behavioral information, effect of any type of pharmaceutical intervention and also any other effect of an external agent therapy, or Brain Machine Interface (BCI) on the brain. As used herein, the term "therapy" may optionally include the application or use of any type of device, including but not limited to neural stimulators and neuroprostheses at the neural network level.

Optionally and preferably, cortical estimation is used for source localization (from the electrical signal map), whether by using many single trials, many trials on the same person or both. Once cortical estimation has been performed, then the functional meaning may be ascertained, for example including with regard to which part of the brain is involved and also whether there is synchronization, or lack thereof, between areas of the brain.

Once source localization has been determined, then optionally the patterns of such localized sources may optionally be analyzed.

Although the present description centers around the use of EEG data, it should be noted that this is for the purpose of illustration only and is not meant to be limiting in any way. Any type of brain imaging data may optionally be used, including but not limited to CAT (computer-aided tomography) scans, PET (positron emission tomography) scans, magnetic resonance imaging (MRI) and functional magnetic resonance imaging (fMRI), ultrasound, MEG (magnetoencephalography) and single photon emission computed tomography (SPECT), invasive Brain Machine Interface (BCI) and neuroprostheses at the neural level, or any other noninvasive or invasive method and/or combinations thereof. Optionally, a plurality of different types of data may be combined for determining one or more patterns as described herein. A stimulus or stimuli may also optionally be applied as described above for EEG data.

However, the use of EEG or event related potential (ERP) for sampling as it relates to flow patterning has the advantage of high temporal resolution (in the millisecond range) (as does MEG, but which is significantly more expensive). While the tradeoff is in spatial resolution, from a neurophysiological perspective, while looking for temporal patterns, the temporal resolution is more critical. Spatial resolution of several $cm^2$ may be very informative in neuropsychological terms. Furthermore, neighboring regions in the brain generally tend to act in a relatively synchronous manner and therefore compromise in spatial resolution is often satisfactory for experimental or clinical purposes.

According to some embodiments of the present invention, preferably one or more of the following methods may be applied for processing EEG data. For example, heuristic thresholds for clustering in different band passes may optionally be applied. Optionally and preferably, data from fragments of trials may be incorporated into patterns.

According to some embodiments of the present invention, there is provided a method for analyzing neurophysiological data, the method comprising: obtaining EEG signals from multiple subjects for a particular behavioral process; analyzing the EEG signals, wherein the analyzing comprises at least one or both of bandwidth or bandpass filtering; and identifying patterns of brain activity for the behavioral process for the research groups according to the analyzed signals.

Optionally, the bandwidth or bandpass filtering comprises applying a plurality of overlapping filters. Also optionally, the analyzing the EEG signals further comprises applying a threshold to the signals. Preferably, the threshold provides a cut-off for noise filtration.

Optionally, the obtaining the EEG signals comprises obtaining EEG signals from spontaneous brain activity. Preferably, the spontaneous brain activity occurs through interaction of each subject with a surrounding environment.

Optionally, the obtaining the EEG signals comprises obtaining EEG signals before, during or after performing a task, or a combination thereof. Preferably, the obtaining the EEG signals is performed with a continuous EEG for at least a plurality of minutes. More preferably, the task comprises a plurality of tasks. Most preferably, the task is selected from the group consisting of lower level cognitive tasks and higher level cognitive tasks.

Optionally, the analyzing the EEG signals further comprises discretizing the EEG signals according to latency, amplitude and frequency to form a plurality of events. Preferably, the analyzing the EEG signals further comprises clustering the events to form a plurality of clusters. More preferably, the clustering further comprises determining a minimum number of events required to form a cluster; and accepting a cluster only if the cluster contains the minimum number of events. Most preferably, the clustering further comprises determining a causality between the clusters.

Also most preferably, the clustering the events is determined according to an amount of permitted variance within each cluster. Optionally and most preferably, the clustering the events is determined according to an amount of permitted variance between clusters.

Optionally and most preferably, the clustering the events further comprises comparing clustered events to a previously determined pattern. Optionally, the comparing the clustered events comprises searching through a plurality of previously determined patterns and selecting a closest pattern.

Preferably, the analyzing the EEG signals further comprises determining a distance from an EEG electrode providing each signal; and weighting each event according to the distance.

Optionally and preferably, the analyzing the EEG signals further comprises combining a collection of a plurality of clusters to form an activity network. More preferably, the identifying the patterns comprises identifying source localization for the activity network. Most preferably, the identifying the source localization is performed according to LORETA (low resolution electromagnetic tomography).

Most preferably, the identifying the patterns further comprises analyzing source localizations for the activity network to identify at least one pattern or to compare the source localizations to a known pattern, or a combination thereof.

Optionally and most preferably, the identifying the patterns further comprises determining a functional brain activity correlation to the source localization. Also most preferably, the functional brain activity correlation comprises determining synchronization, or lack thereof, between a plurality of areas of the brain.

Optionally, the identifying the patterns further comprises eliminating at least one pattern. Preferably, the at least one pattern is eliminated according to complementarity to at least one other pattern.

Optionally, the EEG signals are obtained from a single trial on each of the multiple subjects.

Optionally and alternatively, the EEG signals are obtained from a plurality of trials on each of the multiple subjects.

According to other embodiments of the present invention, there is provided a method for decomposing an EEG, comprising: Obtaining signals for the EEG; Decomposing each EEG signal according to wavelet analysis to identify a waveform; and Extracting a waveform essence of the EEG.

According to still other embodiments of the present invention, there is provided a method for analyzing neurophysiological data, the method comprising: obtaining EEG signals from multiple subjects from one or more research group for a particular behavioral process; identifying sets of patterns of brain activity for the behavioral process for the research groups; and localizing sources of activity participating in the particular behavioral process for the research groups.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which:

FIGS. 5A-5C show signal feature identification for an actual EEG signal;

FIG. 7A shows hypothetical data obtained from four elements, while

Figure 1:
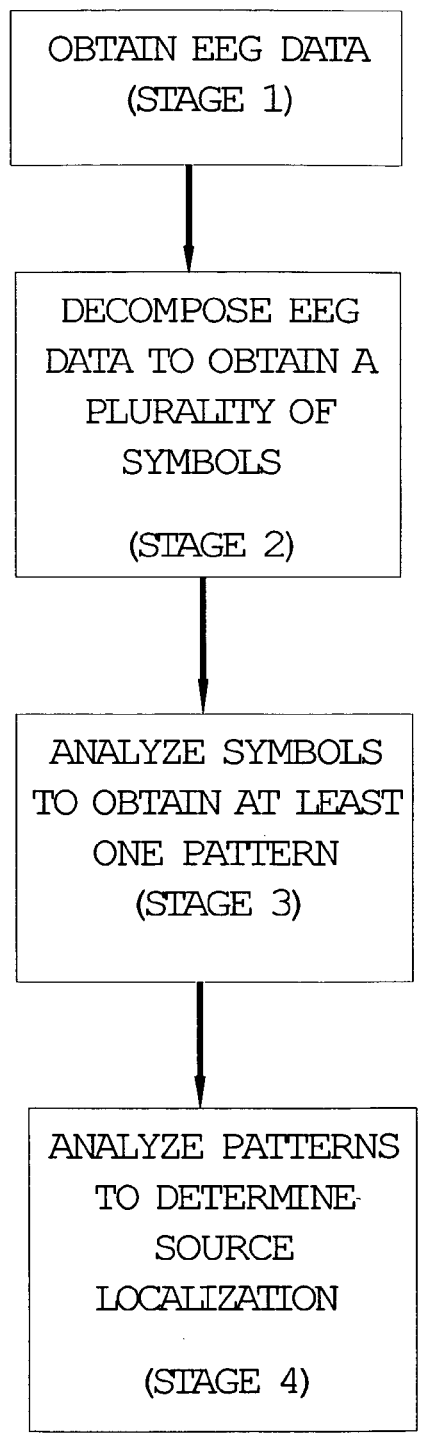
FIG. 1 is a flow chart diagram illustration of an overview of a method of functional analysis of neurophysiological data, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The method of the present invention features decomposing neurophysiological data to form a plurality of signal features. As described herein as a non-limiting, illustrative example only, the method of the present invention is described with regard to EEG data.

EEG data is preferably collected in response to a stimulus or stimuli, such that signals are obtained from the subject before and after the application of the stimulus or stimuli. The stimulus or stimuli may optionally comprise any type of task and/or action, including conceptual tasks and/or actions (the latter may optionally be used with any subject but are preferred when the subject is suffering from some type of physical and/or cognitive deficit that may prevent actual execution of a task and/or action, as for example may be seen in response to various brain injuries such as stroke). The EEG data is then decomposed to form a plurality of signal features, which relate to the brain activity or activities generating the signal(s).

Decomposition of EEG data preferably includes waveform analysis. Conventional waveform analysis is performed by examining the pattern of peaks; however, this method is flawed, because the true generator (i.e., brain and/or external neural location which produced the wave) is not known. According to preferred embodiments, the method of the present invention uses wavelet analysis and bandpass/bandwidth filtering to locate underlying aspects of the wave, such that the wave is decomposed to a plurality of overlapping sets of signal peaks which together make up the waveform. The filters themselves may optionally be overlapping. Even if the bandpass cutoff is not defined correctly, the preferred examination of data from a plurality of subjects results in identification only of repetitive peaks that make up the waveform. Such analysis may optionally be performed after the subject has been subjected to a stimulus or stimuli; if no such stimulus/stimuli are provided, then optionally a predetermined template may be provided and applied to the signals as described herein.

These methods overcome drawbacks of the background art for decomposition of EEG data, which include poor characterization of the elementary waveforms which span the sampled recording. A discrete set of such elementary waveforms, which is both orthogonal and well established in neurophysiology, is not attainable. Furthermore, according to background art methods, the waveforms are not characterized in a sufficiently effective discrete manner with sufficiently simple identifiers through which complex repetitions over subjects could be identified.

The use of multiple trials (i.e., repeated testing a single subject) preferably overcomes these drawbacks of the background art, although such multiple trials are not required in all instances.

Next, the decomposition of the EEG data preferably continues through extraction of waveform essences. Once the correct set of one or more bandpass filters is selected, if the EEG signal peak is symmetric, only the time required for the peak to be reached ("time to peak") and its height/amplitude are needed for further analysis. For non-symmetric peaks, an additional one or more bandpass filters are required to find symmetric peaks. These are waveform essences, and feature three vectors (time, amplitude and the identity of the bandpass filter itself) for each electrode. These three vectors are used to select or form the signal features, and/or are the signal features themselves.

The signal features are preferably arranged as a time series, showing how the output of each electrode changes over time. Such a change over time is also preferably analyzed as part of the signal feature analysis, described in greater detail below.

The signal features may then optionally be analyzed to determine one or more patterns, which may then in turn optionally be combined to form more comprehensive patterns.

The patterns may optionally be identified through a raster plot, featuring results from a plurality of subjects, for example for a particular electrode or combination of electrodes, with the application of a particular bandpass and/or bandwidth filter. For example, the bandpass could optionally feature a threshold cut-off. Other methods for pattern identification include but are not limited to clustering, use of a template and/or application of one or more heuristic methods.

Once the one or more patterns have been determined, preferably localization for the EEG signals is determined. Such localization is preferably determined according to a likelihood method.

The principles and operation of methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Reference is now made to FIG. 1, which is a flow chart diagram illustration of an overview for functional analysis of neurophysiological data, in accordance with embodiments of the present invention.

In stage 1, EEG data is obtained as is known in the art. For obtaining such data, a subject has an array of electrodes placed on his or her head. The electrodes may optionally feature nanostructures such as carbon nanotubes (or other such suitable material(s)), or any type of MEMS (Micro-Electro-Mechanical Systems) electrodes as is known in the art, for contacting or being inserted into the scalp, for a more sensitive reading. Non-contact electrodes may also optionally be used. Each electrode is connected to one input of a differential amplifier (one amplifier per pair of electrodes); a common system reference electrode is connected to the other input of each differential amplifier. These amplifiers amplify the voltage between the active electrode and the reference. For the purpose of the present invention, the EEG signal is assumed to be collected through digital EEG, such that the amplified signal passes through an analog-to-digital converter. Different sampling rates are possible for the converter. As is known in the art, the correct (or at least a suitable) sampling rate and voltage amplification should be selected according to the task. For example, for a rapidly performed task, then preferably a quick sampling rate and high amplification are selected. Also the number and spacing of electrodes are selected as appropriate for the task.

The electrical communication between the electrodes and the amplifier may optionally be performed through wires, but can also be wireless. The placement of the electrodes on the scalp may optionally be determined according to known methods. For example, a 10-20 EEG system may optionally be used, with activity recording from multiple locations, with a reference electrode and a ground. In some embodiments, eye movements (EOG) and muscle movements, and/or subthreshold activity (myopotential measurements instead of actual movements), are recorded as well.

Optionally and preferably, the subject is presented with a stimulus or a set of stimuli, and activity is recorded during a response to the stimulus or stimuli. As noted above, the stimulus or stimuli are optionally simple (for example provision of a single audible sound) or complex (a cognitively demanding task). Also the stimulus or stimuli may optionally require performance of an actual action and/or task or alternatively may be conceptual in nature.

In alternative embodiments, the subject is not presented with particular stimuli and responses, and activity is recorded during "spontaneous activity" or during particular activities. Many such protocols of stimuli, stimuli-responses, action-related and "spontaneous" activity are known in the art, and may include any stimulus-response neuropsychological tests such as the Stoop task, the Wisconsin card sorting test, etc; tests may include stimulus-only based tests such as mismatch negativity, BERA (brain-stem-evoked response audiometry), etc; they may include response-only based tests, such as saccade analysis, MRP (movement related potentials), N-back memory tasks and other working memory tasks, the "serial seven" test (counting back from 100 in jumps of seven), and Posner attention tasks etc; and they may optionally include "spontaneous" activity.

Additionally or alternatively, the subject is tested in a non-laboratory or "natural" environment. Also additionally or alternatively, the subject is ambulatory during testing. The type(s) of tests performed may optionally comprise "spontaneous activity", particular stimuli and responses, particular actions and/or tasks, or a combination thereof.

The EEG digitized signals are optionally filtered before decomposition. Non-limiting examples of suitable filters include but are not limited to a high pass filter, a low pass filter and a "notch" filter, to account for the effect of power lines. Preferably, no filters are required to eliminate "noise" because multiple repetitions are averaged, such that true "noise" is eliminated as it is random. However, such filters may optionally be used and are preferably used for single trials in a single subject.

In some embodiments, only single trials are used. In some embodiments, continuous input (i.e. a continuous stimulus or stimuli) may be used. For continuous input, optionally data may be acquired as a continuous stream where signal properties and/or event codes are used to identify stimulus onset.

In stage 2, the EEG data is decomposed to form a plurality of signal features. The elementary events for the time-series could be filtered waveforms, wavelets, markers of wave amplitudes, etc.

In stage 3, the signal features are analyzed to form one or more patterns. Such an analysis may optionally include arranging the signal features as a time-series for each subject, although preferably this process is performed only for signal features obtained as the result of provision of a stimulus or stimuli to the subject.

In stage 4, the patterns are analyzed to determine source localization. It should be noted that in this embodiment the focus upon regions which repetitively participate in patterns over many subjects in research groups enables correction of inaccurate source localizations. For example, if an activity is "smeared" in one subject from region A to a neighboring region B, but consistently occurs in region A on many subjects of the research group, only region A will occur in a pattern.

Optionally improved source localization and analysis of spatiotemporal patterns are performed, by posing constraints regarding possible signaling in particular areas according to other types of data, such as data obtained through other types of brain imaging and so forth.

Figure 2:
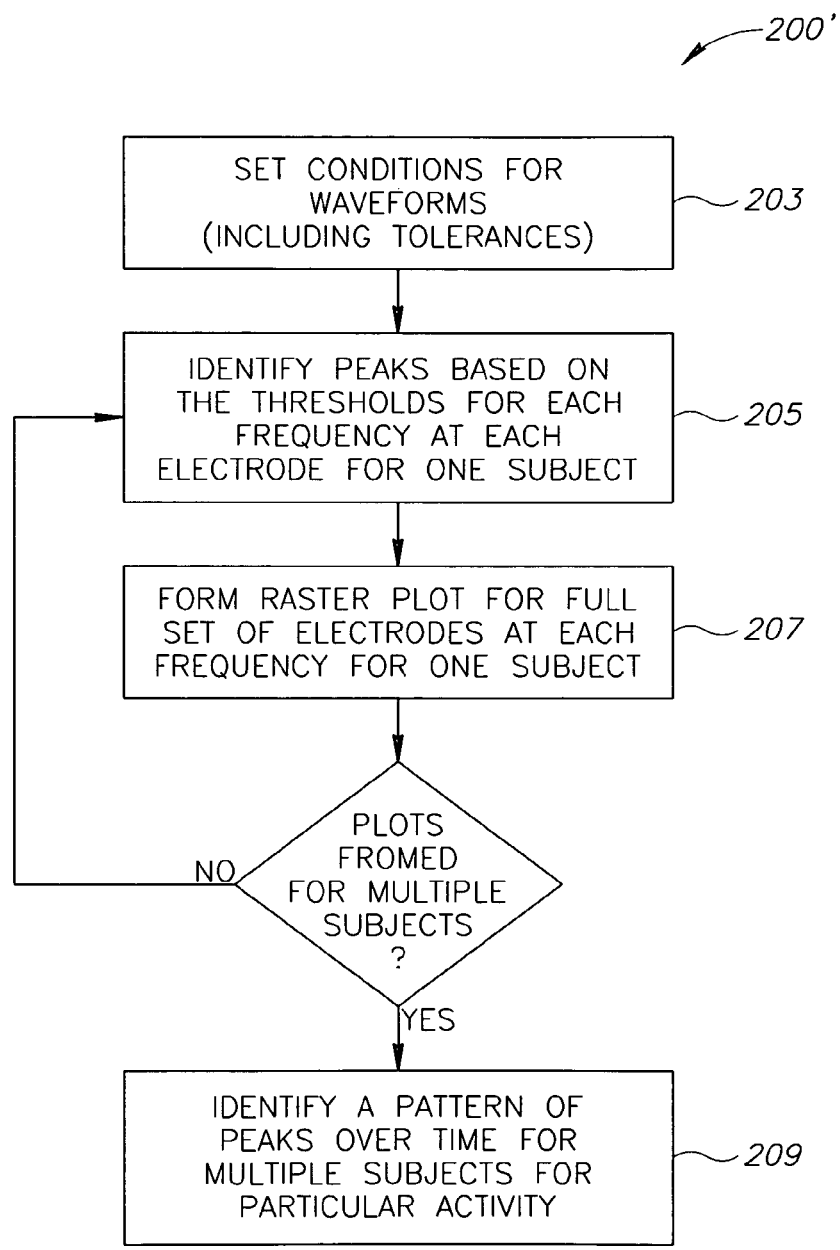
FIG. 2 is a flow chart diagram illustration of a method of pattern analysis, in accordance with an embodiment of the present invention wherein pattern analysis is performed prior to source localization.
Figure 3:
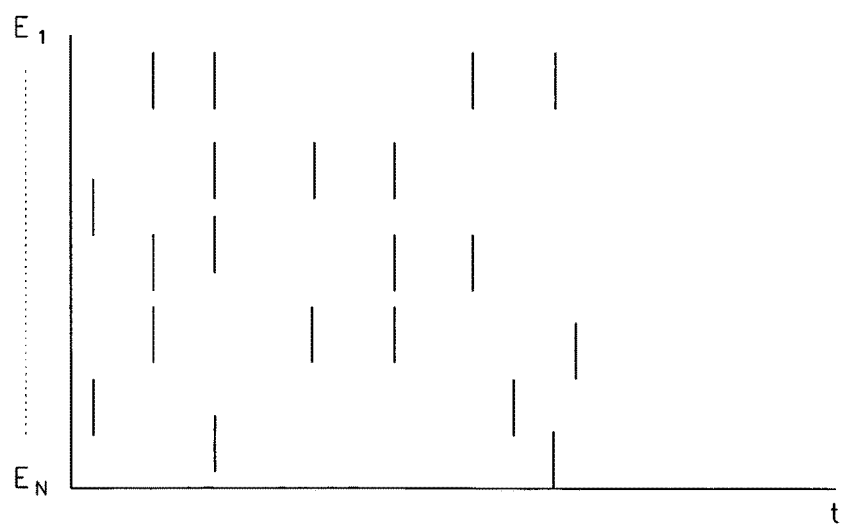
FIG. 3 is a graphical illustration of a raster plot, which serves as a basis of the pattern analysis of FIG. 2.

Reference is now made to FIG. 2 and FIG. 3 taken together, where FIG. 2 is a flow chart diagram illustration of a method of pattern analysis 200', in accordance with another embodiment of the present invention wherein pattern analysis is performed prior to source localization, and is performed on waveforms directly obtained from the electrodes, (or any other chosen characteristic of the sampled activity), and FIG. 3 is a graphical illustration of a raster plot, which serves as the basis of pattern analysis 200', as will be described hereinbelow.

First, one or more conditions (such as thresholds) for waveforms obtained from the electrodes (stage 203). In one embodiment, a binary type of threshold is used, wherein peak values above the threshold are included and values below the threshold are excluded. In another embodiment, a gradual scale may be included. As stated, not only peaks, but also wavelets, or other discrete identifiable elements for each electrode for the particular subject could be utilized. In one embodiment, waveforms which are of varying frequencies are separated out, and peaks are identified (stage 205) for each frequency at each electrode for each subject. This stage is repeated for all electrodes per subject.

Next in stage 207, a raster plot for the full set of electrodes showing peaks over time. An example of a raster plot is depicted in FIG. 3. It should be noted that tolerances for time may be included as well, such that if the peak occurred within the determined tolerance it will be counted. It should further be noted that patterns may be identified from combined activities at different peaks. Furthermore, the combinations of synchronous activities at different frequencies may enable more precise description of the waveform, and may more closely relate to the actual neural pattern. These stages are preferably repeated over multiple subjects and the results of the peak identification of multiple subjects over various frequencies over time are input into a processor which is configured to identify (stage 209) a pattern of peaks over time for multiple subjects for a particular research group. Specifically, a search is performed for repetitive patterns among subjects of the same research group.

The patterns involve the timed activation of sets of electrodes, with temporal, spatial and strength tolerance. This is based upon counting the number of times a particular signal strength is obtained at a particular time period, pairs of such events, and so on to larger and larger groups of such events. Thus, a simple counting method is used to determine a pattern wherein patterns of activation of a set of electrodes, each with its strength/temporal/spatial characteristics that are repetitive among subjects of a certain research group, are identified—all within their dynamic tolerances. It should be readily apparent that the greater the number of inputs (i.e., the number of experimental subjects or trials per subject used), the more robust the pattern analysis will be. Those patterns are later used for comparison, as will be described further hereinbelow. The identified patterns are then sent to source localizer 20 for source localization.

Figure 4:
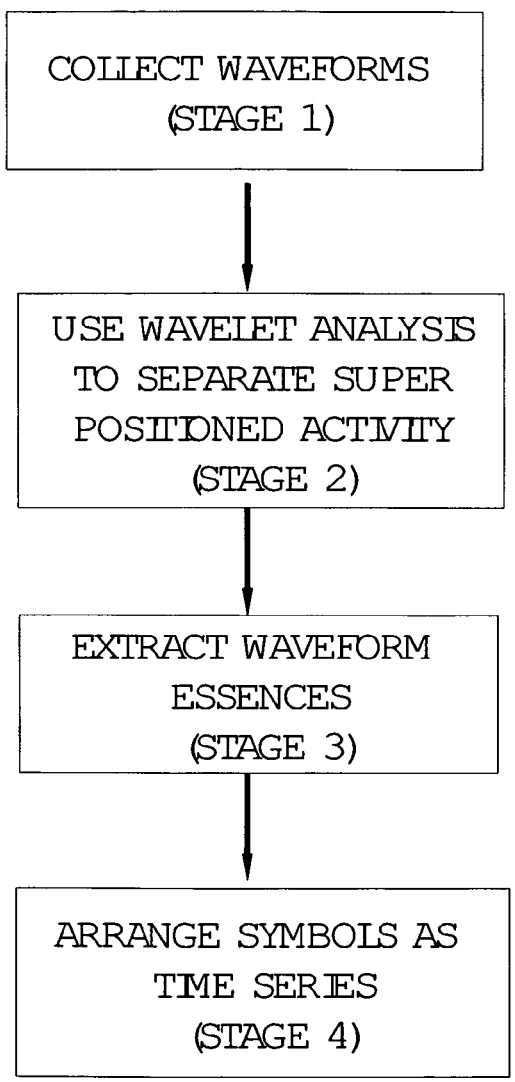
FIG. 4 is a flow chart diagram illustration of a method of identifying signal features, in accordance with an embodiment of the present invention.

Reference is now made to FIG. 4 which is a flow chart diagram illustration of a possible method for identifying one or more signal features, in accordance with an embodiment of the present invention. Waveforms are collected (stage 1) as described above. Each of electrodes $E_1 \ldots E_3$ has its own signal each of which may be at a different strength. The waveform of each signal for each electrode is preferably analyzed separately.

In stage 2, wavelet analysis is preferably used to separate superpositioned activity. Also any other wave characteristic could be used instead of peaks, such as wave envelope shape, etc. Other types of analyses may also optionally be used, such as application of a template (such as an expected form of a sinus wave) to the signals for example.

In stage 3, decomposition of the EEG data preferably continues through extraction of waveform essences. Once the correct set of one or more bandpass filters is selected, if the EEG signal peak is symmetric, only the time required for the peak to be reached ("time to peak") and its height/amplitude may optionally be used. For non-symmetric peaks, an additional one or more bandpass filters are required to find symmetric peaks. These are waveform essences, and feature three vectors (time, amplitude and the identity of the bandpass filter itself) for each electrode. These three vectors are used to select or form the signal features, and/or are the signal features themselves.

In stage 4, the signal features are preferably arranged as a time series, showing how the output of each electrode changes over time. Such a change over time is also preferably analyzed as part of the signal feature analysis, described in greater detail below.

Figure 5A:
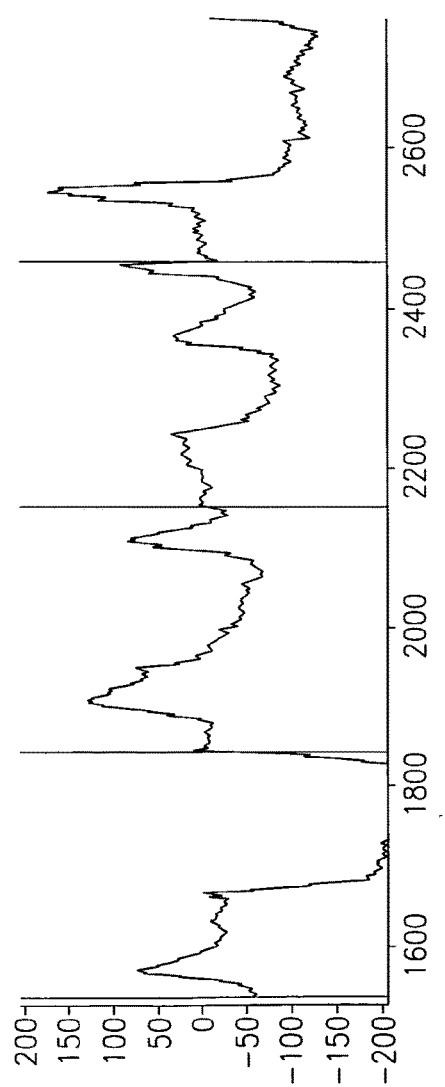
Figure 5B:
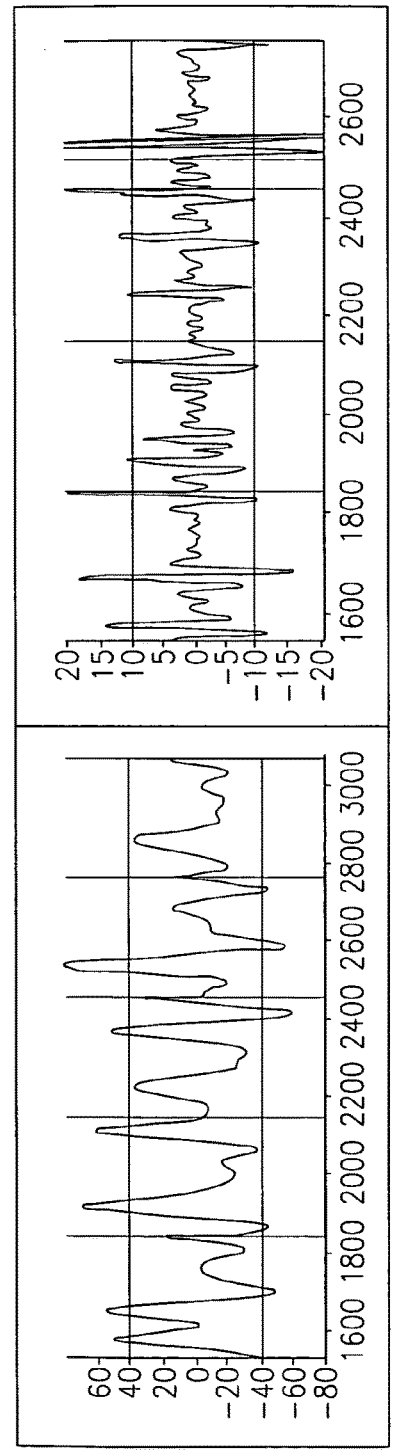

FIGS. 5A-5C show signal feature identification for an actual EEG signal. FIG. 5A shows raw data obtained from a specific electrode during an EEG test, illustrating the electrical potential over time. For this example, the subject received periodic stimulation with a stimulus (although as described above, it is also possible to obtain such data without stimulation). Stimulus presentation times are presented in red.

FIG. 5B shows that activity is then divided into frequency bands—presented are δ (right) and β (left). Amplitude is also divided (horizontal blue line).

FIG. 5C then shows the results. The top row shows the subject identifier (as multiple subjects were tested), epoch (or trial) and type of stimulus. The next row shows the frequency band which was examined, in Hz, showing the minimum and maximum permitted frequencies that were considered. The third row shows time (in milliseconds); the fourth row shows the electrode number (to identify the electrode from which the signal was obtained); and the fifth row shows the amplitude of the signal.

These results collectively form a time series. The time series includes different subjects, trials (epochs) and stimulus types (here left vs. right) as identifiers. The values for the time series are electrode number, frequency, time and amplitude (direction is given by +/−, strength by number of such signs). Such data may also optionally be plotted as a three dimensional chart for each epoch, patient and electrode, with regard to amplitude, frequency and latency (time).

Figure 6:
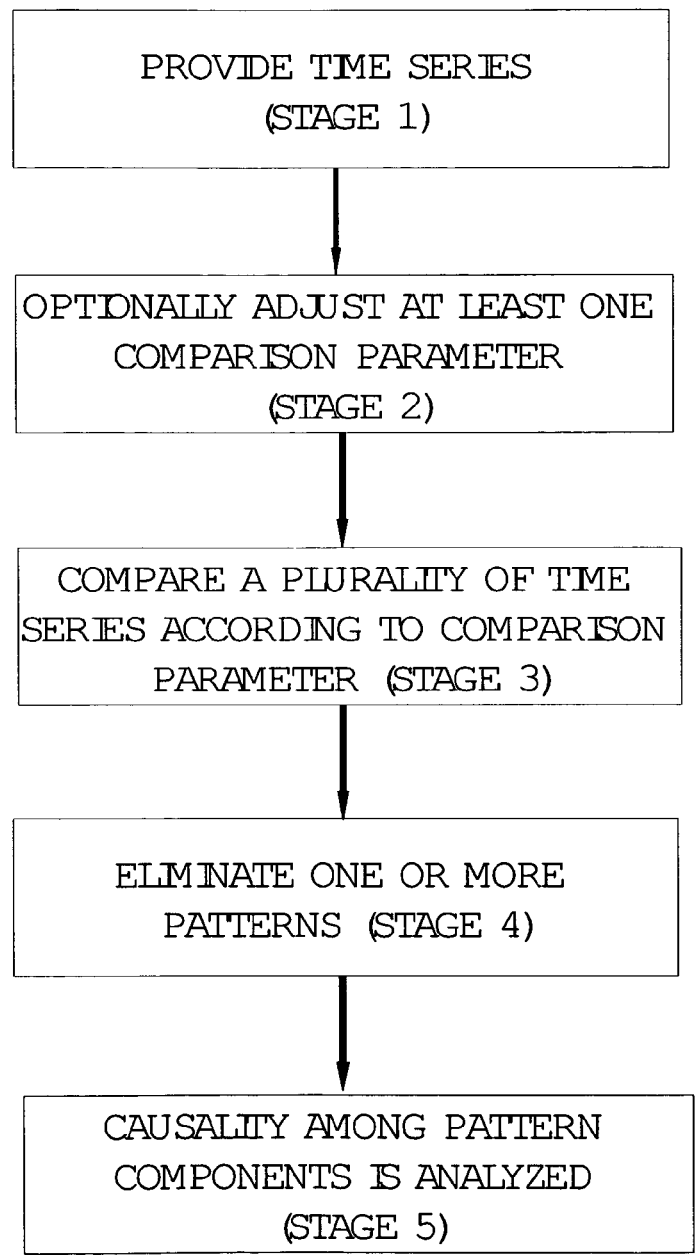
FIG. 6 is a flow chart diagram illustration of a method of analyzing one or more patterns, in accordance with an embodiment of the present invention.

FIG. 6 is a flow chart diagram illustration of a method of analyzing one or more patterns, in accordance with an embodiment of the present invention.

As shown, in stage 1, a plurality of the previously described time series is provided. In stage 2, at least one comparison parameter is optionally and preferably adjusted. The comparison parameter determines the tolerance for a difference between two time series, which would still permit the two (or more) time series to be determined to be a match. The tolerance may optionally be provided in one or more of time, frequency and/or amplitude. Tolerance for timing is preferably continuous, while timing for amplitude is preferably based on the division of amplitude values to discrete ranges.

In stage 3, a plurality of time series is preferably compared according to the comparison parameter. Optionally such comparison could include grouping the time series according to various parameters, including but not limited to one or more of statistical significance, group prevalence, pattern size in terms of participating elements, and so forth.

A non-limiting illustrative method for determining the statistical relevance of a plurality of patterns may optionally be performed as described herein, with regard to a combinatorial test for evaluation of significance of the number of discriminatory patterns. The example for this test relates to an experiment in which two groups are being compared.

Let the discriminatory level be defined as the difference in the number of individuals positive for a certain pattern between the two groups. Let 'd' denote this number. Let the number of individuals tested be 'n1' for the first group and 'n2' for the second group. Let 'Sum' denote the number of individuals (from both groups) for which a certain pattern was positive. Suppose, that $d \geq 7$ is chosen, for an experiment in which n1=n2=10.

The combinatorial number of possible bit vectors for which $d \geq 7$ is possible for this experiment is calculated. In this case the number is 2702. {The calculation sums the values of (n1 over A)*(n2 over B)*2—which stands for all the permutation in which A individuals are positive from n1, and B from n2. In addition—this value is multiplied by 2 from symmetrical reasons—i.e. it does not matter whether group A has 7 positive signals and group B has 0 or vice versa. In case it is important (e.g. a comparisons of Experimental or Treatment vs. Control groups) this value should not be multiplied by 2}.

Let $\Omega$ denote the space of bit vectors options for which 'Sum' can produce results of d>=7. In this specific case $\Omega=\{7 \leq Sum \leq 13\}$. Now, the expected frequency of bit vectors for which $d \geq 7$ out of the space $\Omega$ is estimated. Let this frequency be denoted as P7. Accordingly $p7=N(\{d \geq 7\})/N(\Omega)$.

Let 'k' denote the actual number of patterns for which $\{7 \leq Sum \leq 13\}$. Let 'Xk' be the number of actual patterns for which $d \geq 7$. The distribution of Xk is assumed to be binomial: $Xk \sim Bin(k, p7)$. The p value is measured as $Pr(Xk \geq bin(k, p7))$. This test will produce the cumulative probability of getting a number between 0 and Xk, whereas we need the cumulative probability of getting Xk or more. Hence the p value will be 1−(probability given by the test). The test has certain assumptions. For example, all the possible patterns are assumed to have been given by the algorithm without filtering. Also it is assumed that there is independence between patterns and bit vector division between the two groups under the null distribution.

In stage 4, optionally one or more patterns are eliminated (such an elimination process could optionally also be performed between stages 1 and 2 for example, and/or before stage 3, for example). Non-limiting examples of patterns which are preferably include patterns that distinguish between research groups and/or combinations of patterns which complement one another.

In stage 5, causality among pattern components is optionally and preferably analyzed. For example, optionally a statistical analysis is performed to determine whether the pattern components are likely to be linked in some manner. Automatic evaluation of group thresholds for time, frequency and amplitude is performed by searching for patterns, which occur in some members of the experimental groups, in the data of the other members. For example, if some members of a group exhibit a particular pattern, then preferably data from other members of the group is re-examined in order to determine whether in fact such a pattern exists, even in a more muted form.

Optionally such searching may be performed by placing the portions of patterns (for example source localizations) in a tree and then searching the tree for the best differentiator as cluster criterion.

Figure 7A:
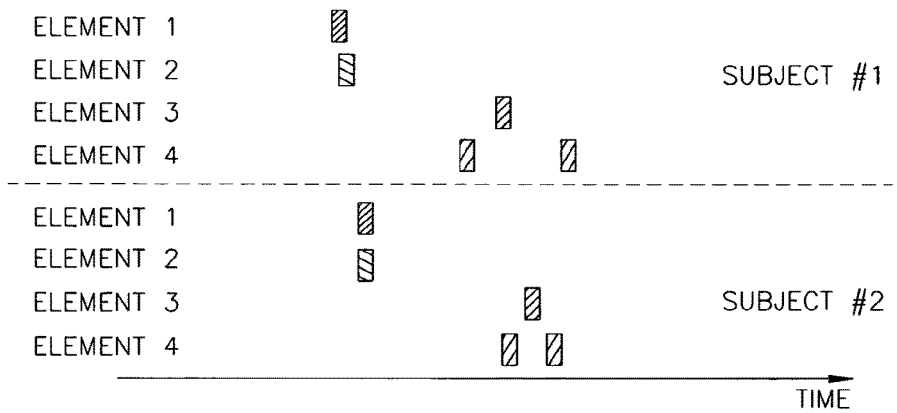

FIG. 7A shows hypothetical data obtained from four elements. These elements are particular electrodes with data analyzed at a particular frequency range at a specific time in a specific strength, presented with four different colors in two different subjects. The activities could be grouped into the same pattern with the relevant tolerance (in this case temporal tolerance).

Figure 7B:
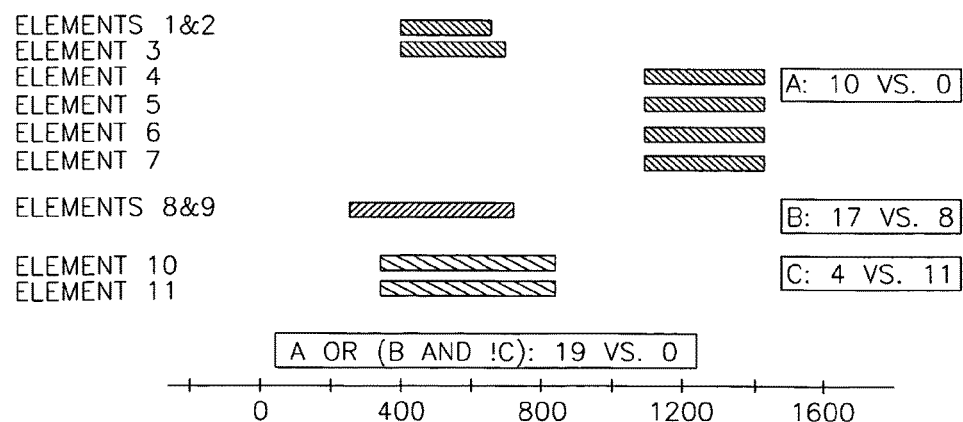
FIG. 7B shows patterns obtained from analysis of actual experimental data.

FIG. 7B shows patterns obtained from analysis of actual experimental data. The analysis results of the dataset identified three patterns, A in green, B in blue and C in red. The elements of the patterns are presented at the Y axis; for each element, temporal tolerance is presented at the X axis (in milliseconds). The numbers near the pattern headers represent their number of occurrences in two experimental groups. Note that while each pattern discriminates between the groups by a given degree, their combination as A OR (B and NOT C) discriminates between the groups completely (each group contains 19 experiments).

Figure 8:
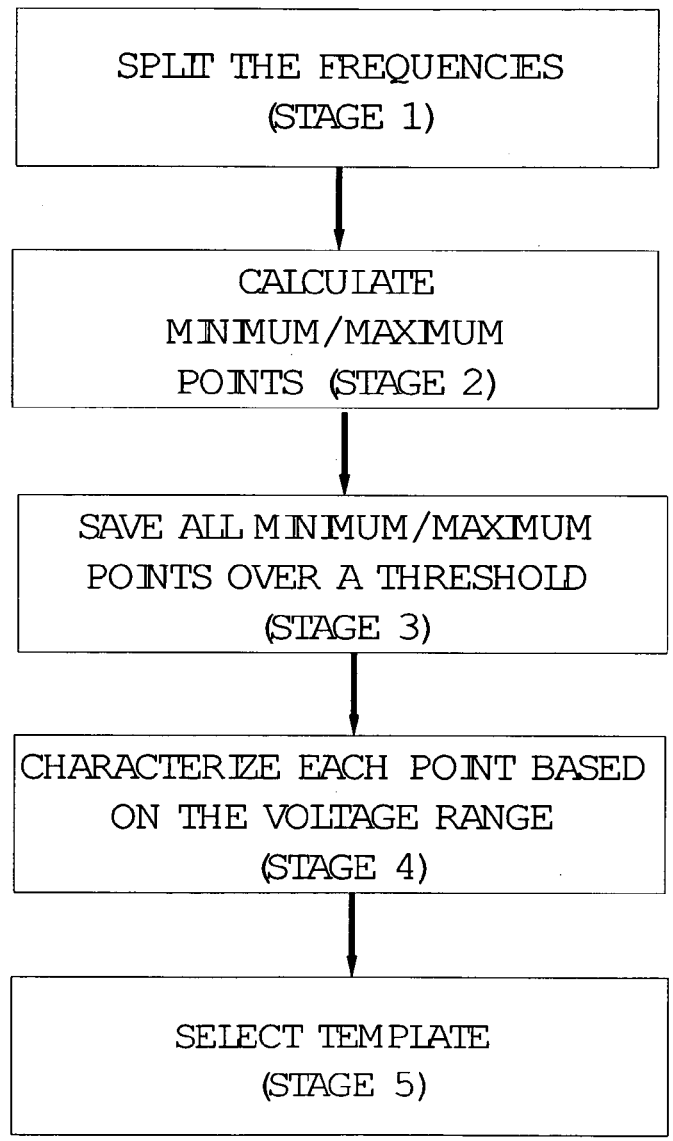
FIG. 8 shows an exemplary method for likelihood analysis for a single trial according to the present invention.

FIG. 8 shows an exemplary method for likelihood analysis for a single trial according to the present invention. In stage 1, the frequencies are split, for example according to spectral Fourier analysis or wavelet transformations.

In stage 2, the minimum and maximum (min max) points are calculated. In stage 3, all min max points that are over a threshold are saved. The threshold preferably depends on the standard deviation.

In stage 4, each point is characterized based on the voltage range where it falls. For example, the simplest characterization is binary such that there are two voltage groups, positive or negative.

In stage 5, preferably a characteristic/representative temporary template that contains the electrode and that has the maximum value of all the electrodes for each sample point is located. Such a temporary template may then optionally be used to characterize the data from a single trial.

FIGS. 9A-D relate to determining a relative order for a plurality of patterns. As described herein, the final output of the pattern-lookup algorithm is a large set of expressions sorted by their score. The score is defined as the difference between the expression's appearance in the first group and the expression's appearance in the second group. However, a plurality of expressions may obtain the maximal score, such that the end-user doesn't know which expressions are most relevant. The illustrative method described herein presents an order over of the set of expressions which will allow the user to efficiently analyze the results presented.

The expressions are ordered and presented by their ability to explain the variance of the entire set of expressions. This is modeled by the similarity index (SI). The similarity index is computed for a specific set of clusters (or single cluster) over the entire set of expressions. For each cluster, a representative expression is found, and the worst distance of that expression to the expressions within its cluster is computed. The representative or typical expression is preferably defined for a cluster of the entire set of expressions. The expression with the shortest distance (the minimal sum of distances) to the rest of the cluster is defined as the representative or typical expression.

From all the worst distances of the clusters in the set, a single average distance is computed. This is the average distance. The similarity index is defined as one minus this distance. This index can vary between 0 (complete identity) and 1 (maximal distance). There is a tradeoff between the number of expressions in a subset of the entire set and the SI. Preferably, the user is able to choose where to draw this line, according to the user's specific needs.

Figure 9A:
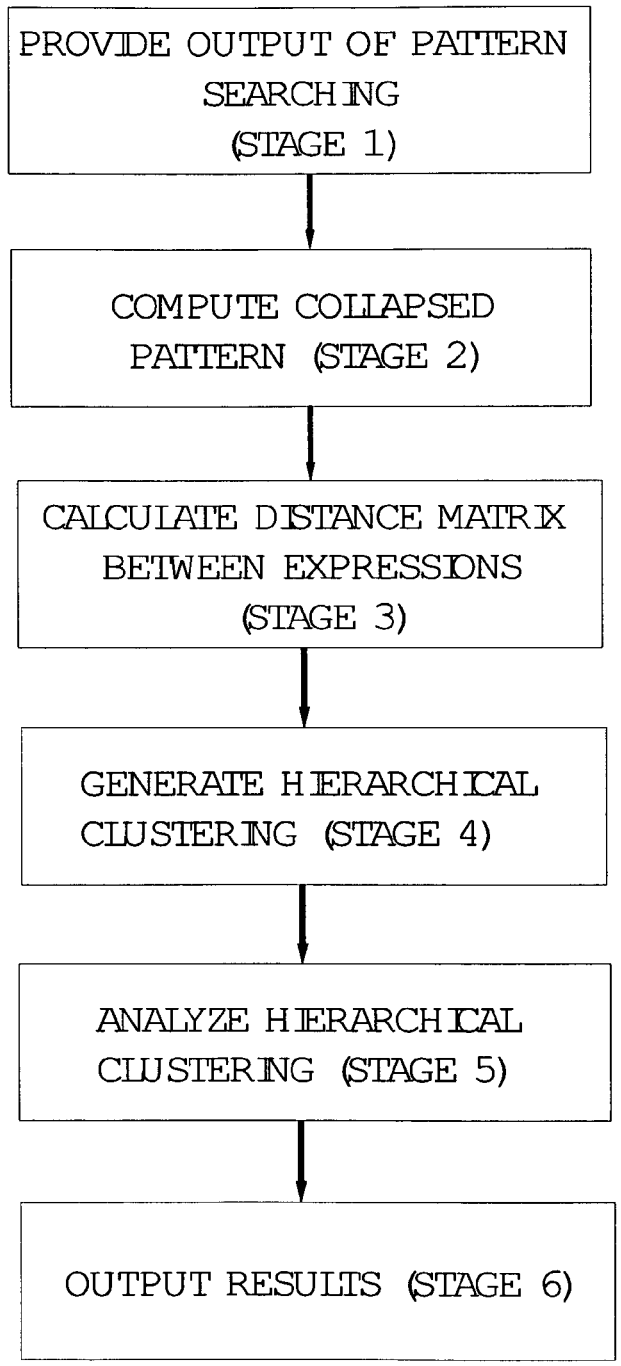
FIGS. 9A-D relate to determining a relative order for a plurality of patterns.

As shown with regard to FIG. 9A, in stage one the output of the pattern searching or "look-up" process is provided. Non-limiting examples of such a pattern searching method are described above. Optionally, the output is converted to another data structure, such as (for example) Matlab data structures (The Mathworks, USA). Note that each expression is comprised of several patterns. These are not specific patterns; rather, they represent a group of bitvector-identical patterns.

For each such group, the collapsed pattern is computed in stage two. The collapsed pattern is the common denominator of all the patterns in the group of bitvector-identical patterns. In order to form this pattern, initially all patterns in the group are transformed from relative to absolute: In a pattern, only the anchor appears in absolute time. The rest of the regions appear in a time relative to the anchor. Each relative time segment is transformed to an absolute time segment in the following manner. Suppose the anchor's time segment is [t1 t2] and the region's time segment is [d1 d2]. The 'absolute' time segment of the region will therefore be [t1+d1 t2+d2]. After this conversion, the absolute-time patterns are then collapsed into a single pattern, such that for each region that appears in any pattern, the common time denominator is computed (the time segment which will include all times of appearance of this region in all patterns). The collapsed pattern is preferably the pattern which is composed of all these regions and time segments.

In stage 3, for N expressions, an <N×N> distance matrix between expressions is calculated. The distance between two expressions is preferably calculated as follows: remove all identical minterms from the two expressions. On the minterms that remain, for all possible permutations of minterms, find the sum of distances between the corresponding collapsed patterns. The minimal sum of all possible sums of the permutations normalized by the number of minterms in the longer expression is the distance between the expressions.

The distance between two collapsed patterns is preferably calculated as follows. Assume there are two patterns, A and B. Because the distance function is directional, it computes the distance from the long pattern (assume A) to the short pattern. For each region in A, the function searches for the identical region in B. If found, the function computes the overlap index—the absolute overlapping time divided by the time the region operated in the long pattern. This is a number between zero and one. This number is added to the overall distance between two patterns. The same process is repeated for every region in the long pattern. The total sum is normalized by the total number of unique regions in both patterns. Again, a number between zero and one is achieved.

Zero would mean no overlap and one would mean complete identity. Therefore, to achieve a distance function, the final number is 1 minus the number we have reached. This is the distance between two patterns.

In stage 4, a hierarchical clustering is generated according to the distances calculated above. In stage 5, the hierarchical clustering is preferably analyzed according to a similarity index (SI) calculation, which is more preferably performed as follows. First, create a cluster set of k clusters (starting from one and incrementing until k equals the number of expressions). The criterion for generation the clusters is the distance. Next, for each cluster formed, find the expression with the shortest average distance to the rest of the expressions in the cluster. This expression is defined as the typical or representative expression of the cluster. For the set of clusters and their corresponding typical expressions, calculate the similarity index (described above).

Figure 9B:
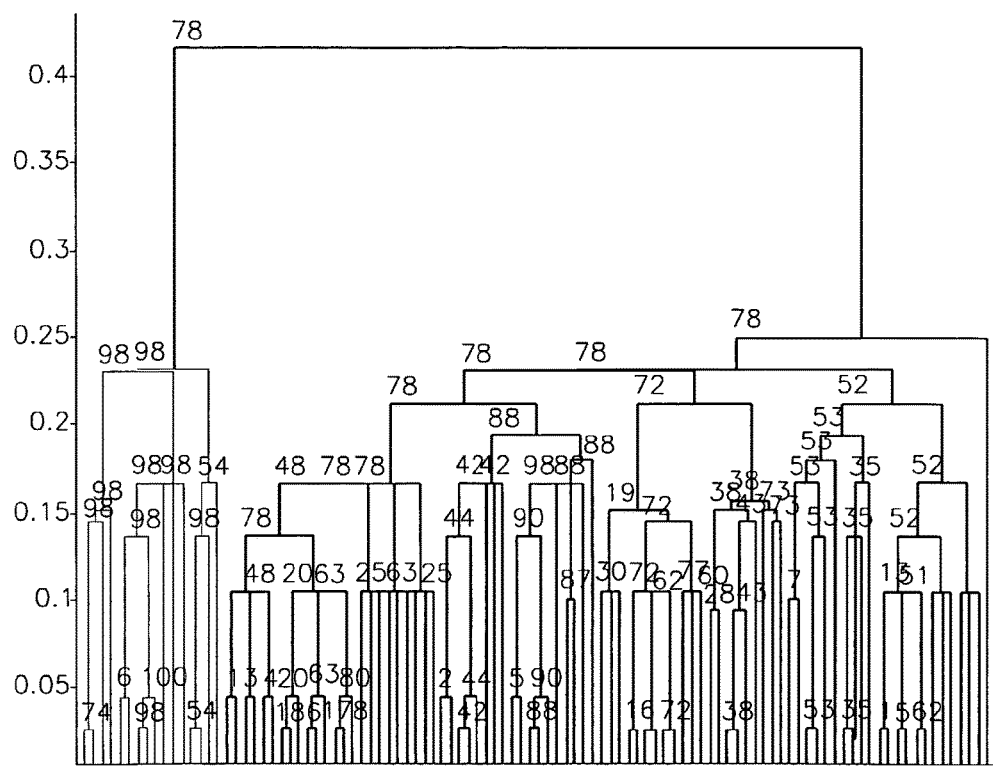
Figure 9C:
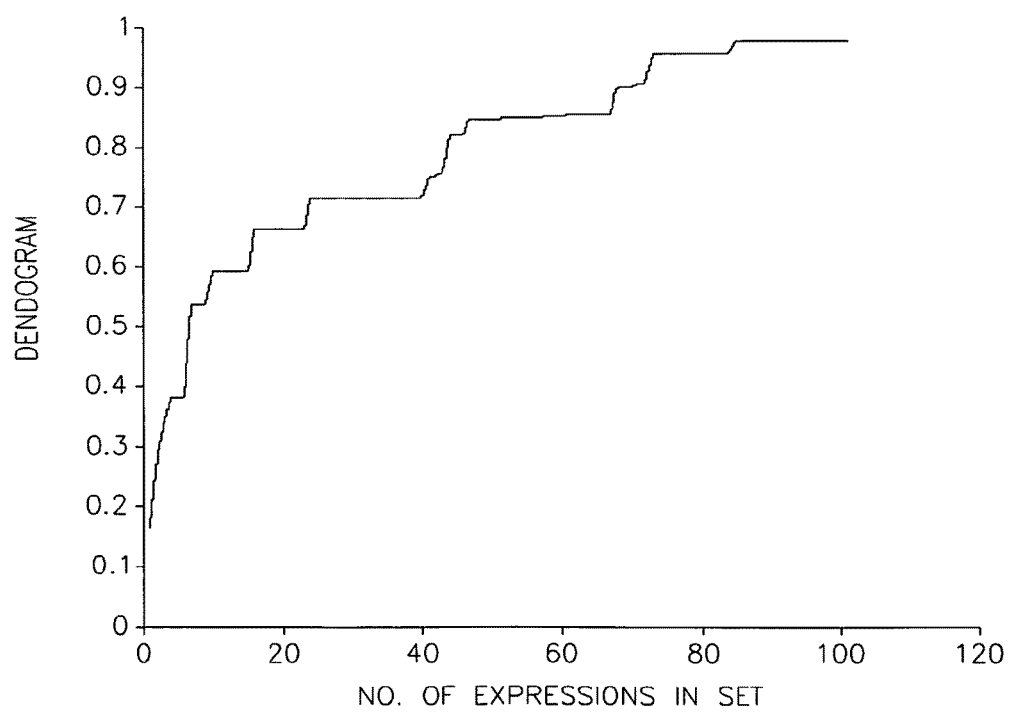
Figure 9D:
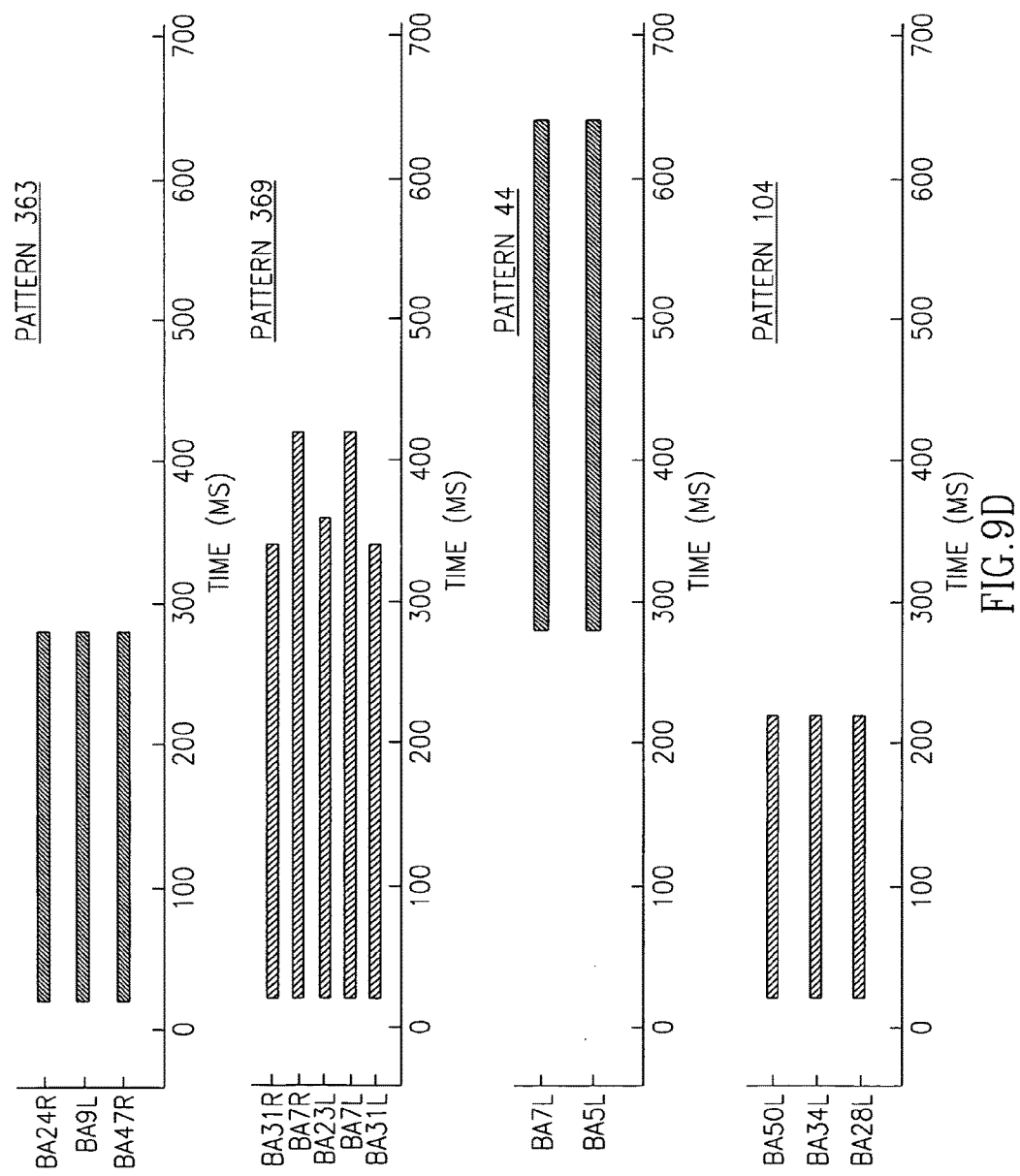

In stage 6, the results are preferably output. Various output displays are possible, as shown for example in FIGS. 9B-D. FIG. 9B shows a dendrogram of the hierarchical clustering with the typical expression on top of each cluster. FIG. 9C presents the SI as a function of the number of clusters (and corresponding typical expressions) in the set. FIG. 9D shows a graphic presentation of the collapsed patterns composing each unique expression in all expression sets.

Of course non-graphic representations are also possible, for example by presenting a data set with the sets of expressions sorted by size. For each set, all expressions are presented. For each expression, all patterns are presented. For each pattern, the collapsed pattern and the best pattern in the BV group are presented. The best pattern is preferably defined over a group of bitvector-identical patterns. It is the longest pattern (region-wise) with the minimal sum of time segments (and therefore can be seen as the most specific).

As previously described, EEG is optionally and preferably filtered before further analysis is performed. Such filtering may also optionally include temporal filtering and discretization, as described in greater detail below.

Figure 10:
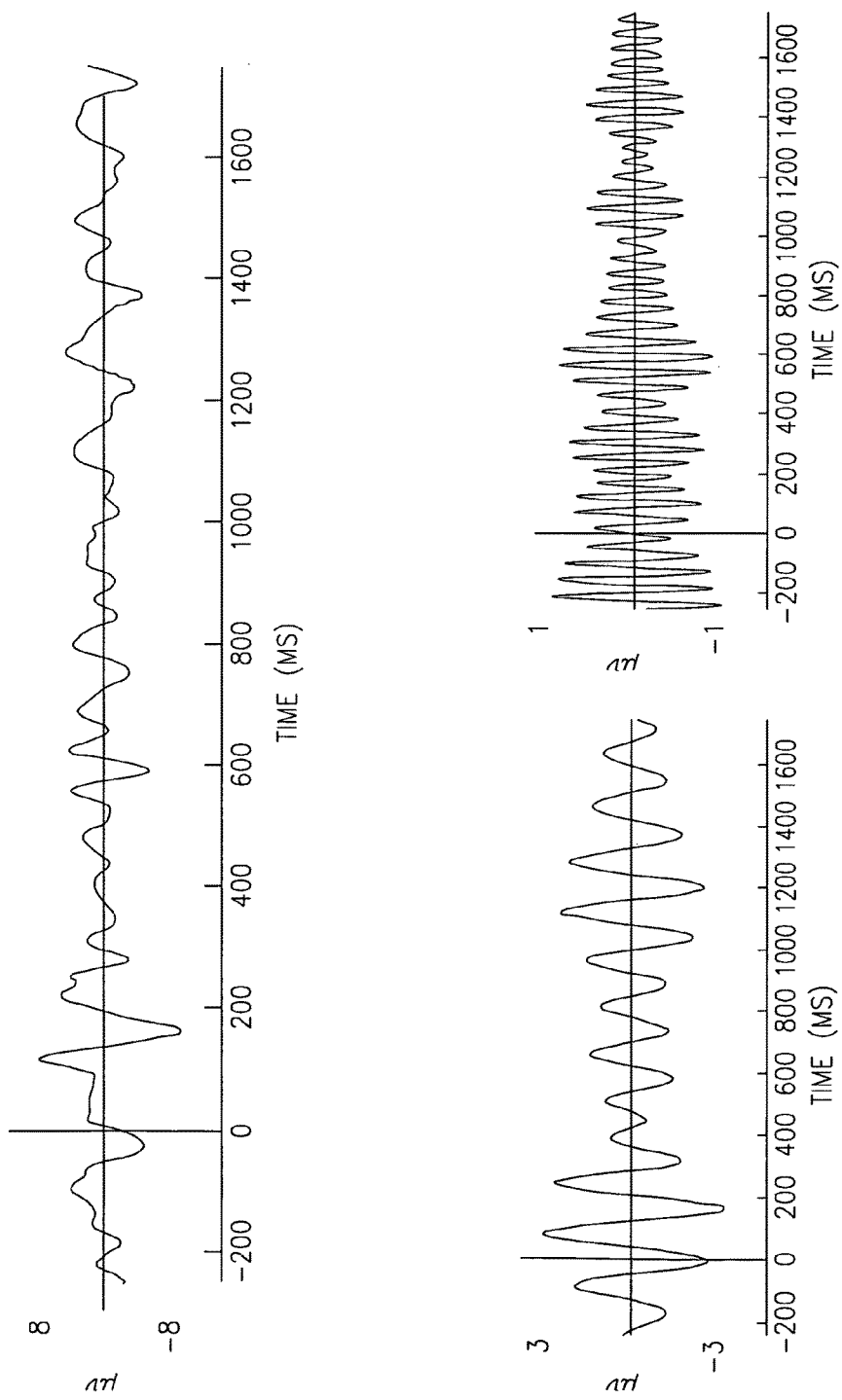
FIG. 10: the top figure presents the activity in electrode P8 in relation to face stimuli (viewing the image of a face, which is a standard type of brain stimulus), while the bottom figures present the filtration of this activity into θ band (5-8 Hz)—left and high β band (17-23 Hz)—right.

Briefly, each electrode in each single epoch is filtered into overlapping frequency bands in order to separate the EEG activity into basic well known brain processes. In the example shown in FIG. 10, the top figure presents the activity in electrode P8 in relation to face stimuli (viewing the image of a face, which is a standard type of brain stimulus). The bottom figures present the filtration of this activity into θ band (5-8 Hz)—left and high β band (17-23 Hz)—right. The frequency bands of filtration are defined parametrically and overlaps are allowed. All overlap frequencies bands are used in the next stages of the analysis so no loss of information is considered.

Figure 11:
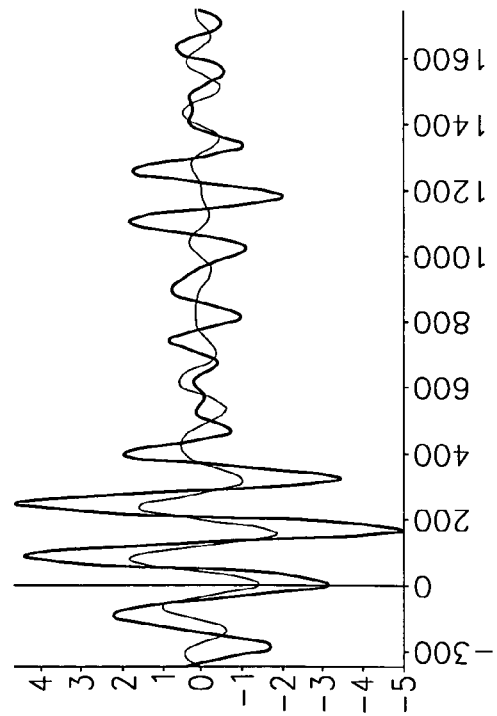
FIG. 11 shows the activity in a single electrode O1 in frequency band 5-8 Hz for two different subjects after face stimulus is presented—one epoch for each subject (one subject is presented in green and the other in blue).
Figure 11:
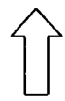
Figure 11:
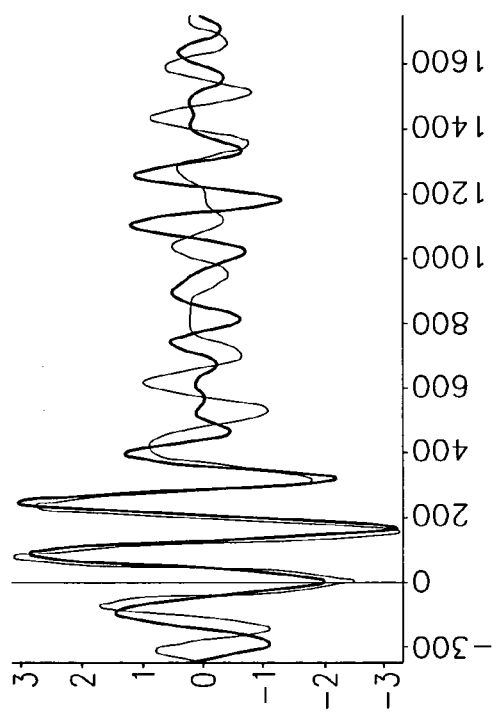

It has been previously demonstrated that the activity measured and the data obtained from individual electrodes may vary significantly between individuals; furthermore, measurements may also vary between electrodes for a single individual. Optionally and preferably, another type of filtering or signal adjustment therefore includes one or more adjustments to overcome this type of variation. Therefore the activity in each electrode is z-score normalized to standardize across subjects. FIG. 11 shows the activity in a single electrode O1 in frequency band 5-8 Hz for two different subjects after face stimulus is presented—one epoch for each subject (one subject is presented in green and the other in blue). At the left, the raw activity is presented for both subjects, while at the right, the Z-score normalized activity is presented. The normalization serves as an equalizer beyond conductivity differences. Also such normalization can increase noisy activity in active electrodes; however, as previously described, it is possible to statistically assume that this noise will be cancelled later in the pattern analysis stage.

Figure 12:
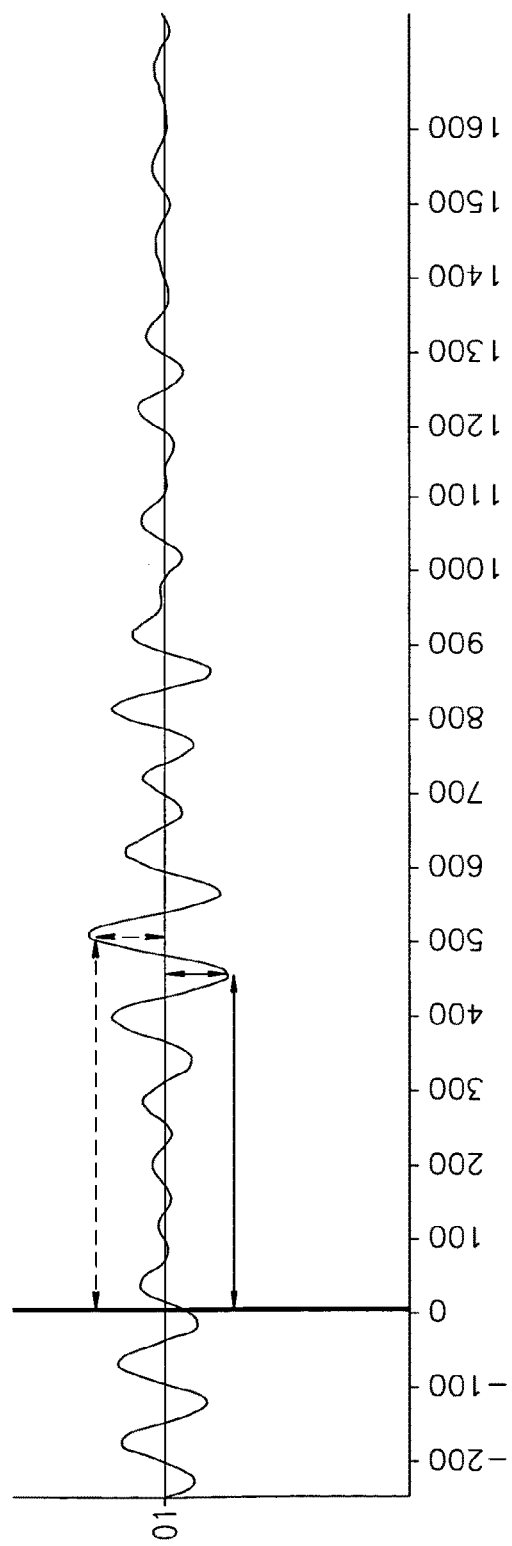
FIG. 12 shows time and amplitude of two waveform peaks.

In the next stage all the local positive and negative peaks of all the filtered signals are found and their latency and amplitude are saved. The activity of a single electrode (e.g. O1 below) for a single epoch in a given frequency band can be then reduced into the times and sizes of the amplitudes of the various waveforms. The activity presented is evoked by face stimulus. The time and amplitude of two waveform peaks are presented in orange (top) and green (bottom) in FIG. 12. Due to the near-symmetry of the waveforms, each waveform is reducible to a pair of numbers denoting the time and amplitude of the waveform peak.

Figure 13:
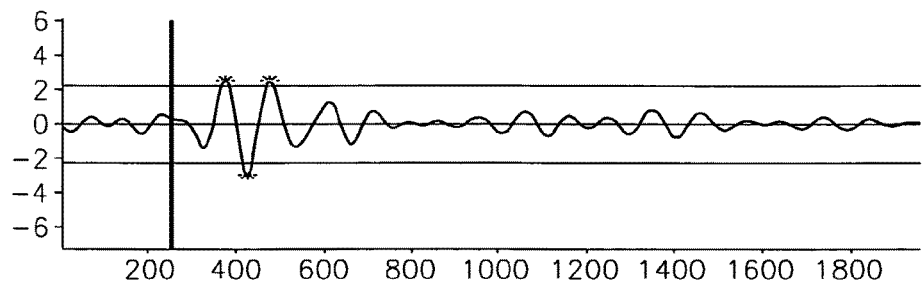
FIG. 13 shows results in three dimensions for two subjects.
Figure 13:
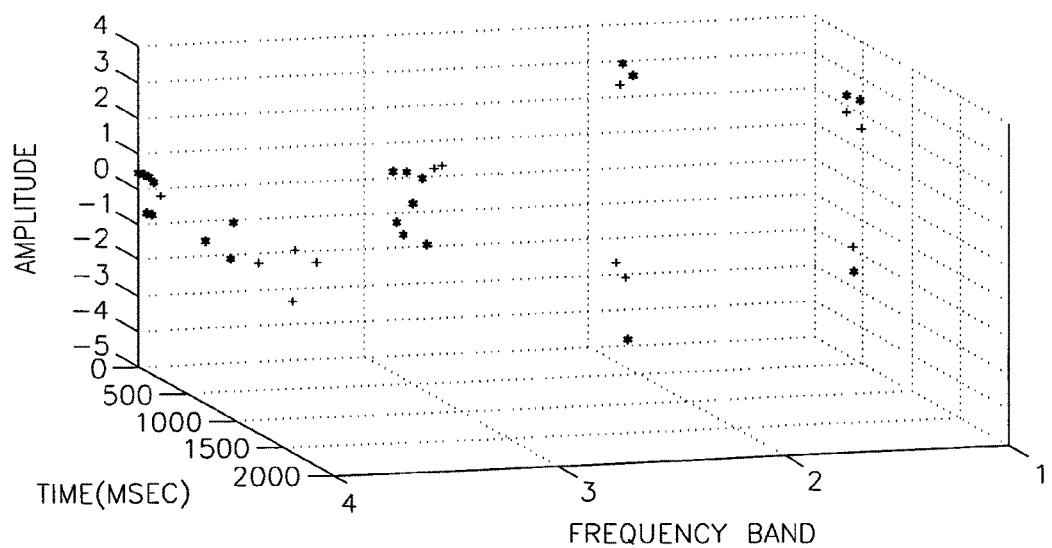

Events can then be described per each electrode and each subject in a 3D space of frequency, latency and amplitude. For example, such results for two subjects are presented in FIG. 13 (bottom). Noise reduction can be done in this stage by using only event with amplitude above some relative threshold for this representation, also as shown in FIG. 13 (top).

EEG signals are then preferably analyzed to determine the relationship between functional events. As previously described, after filtering, clustering is preferably used to determine the relationship between such events. The above time-amplitude-frequency space can be clustered into synchronized events and the relationship between thus combined events can be found. One way to do this is by defined a parametrically moving window over relative time between subjects (and possibly epochs) to scan the delta between pairs of electrode activities to gain repetitive patterns of relative timing. There is preferably some tolerance around the limits of both moving windows to enable the joining or union of similar patterns.

For the purpose of description and without wishing to be limited in any way, the below example centers around combination of events as pairs; however it is also possible to combine events in larger groups (triples, quads, quints and so forth) for larger network relationships.

Figure 14:
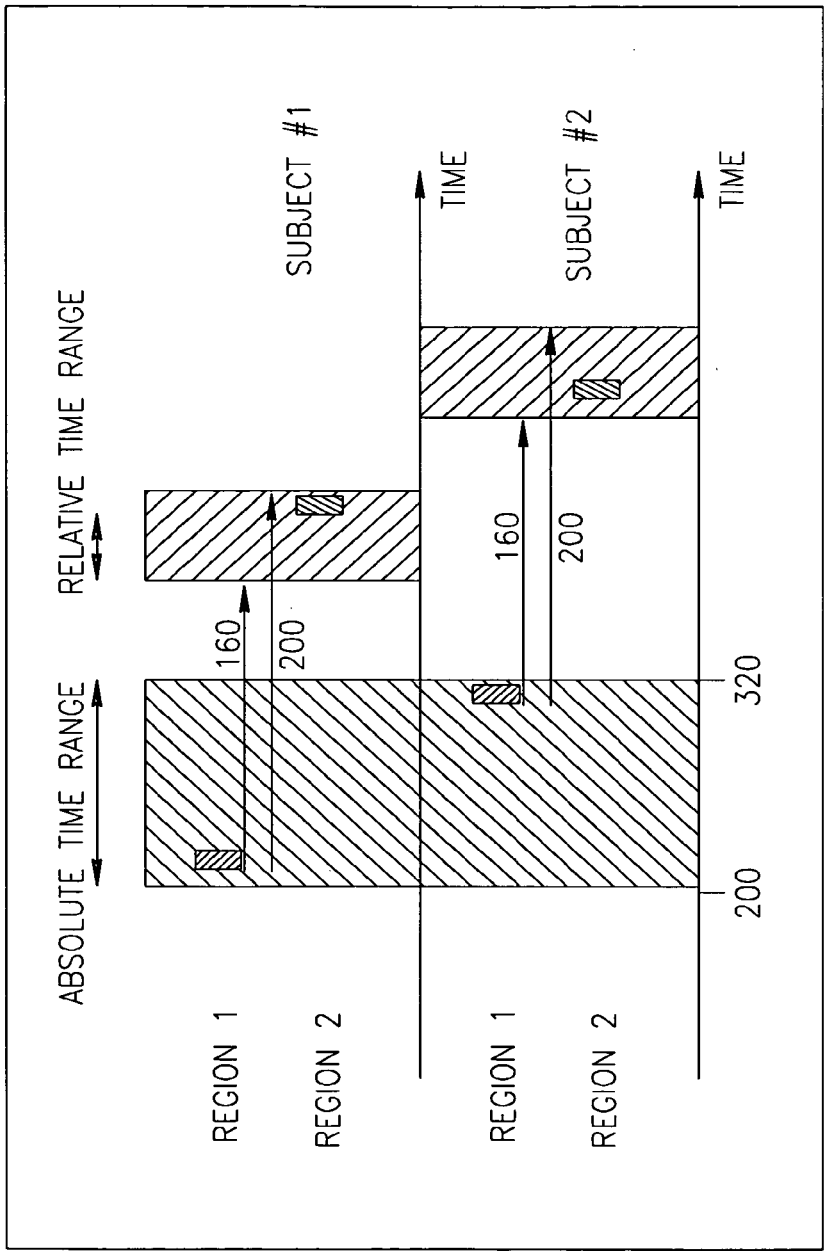
FIG. 14 shows events that have been combined as pairs.

Turning now to the drawing, as shown in FIG. 14, a pair pattern includes: (1) Pair of brain regions; (2) An absolute time range: A range of the absolute activation times of the first region in the pair; (3) A relative time range: A range of the delta times of the second region in the pair; (4) A bit vector, which indicates for each group which subjects in the group had the specified pair pattern; (5) For each group the total number of subjects that had the specified pair pattern.

Figure 15:
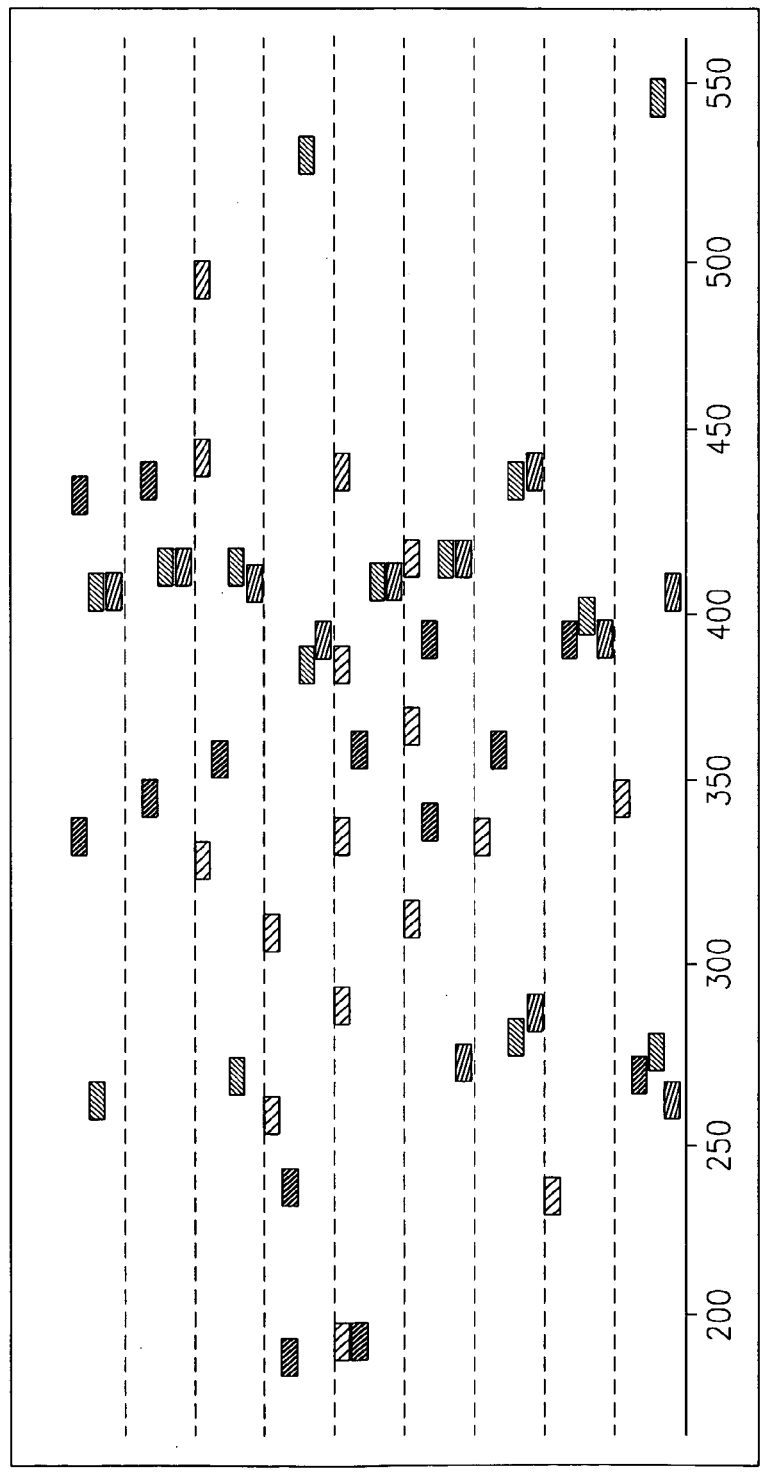
FIG. 15 shows the result of further combinations between pairs of events.

After finding such pairs of synchronized events, preferably one or more pairs are combined into trios etc. by merging pairs that share an overlapping event, optionally until no larger event networks can be found. For example, event times of 4 electrodes P7 (blue), P8 (green), in frequency range 17-23 Hz and O1 (orange), O2 (yellow), in frequency range 5-8 Hz after face stimulus for 9 different subjects. There is variability with regard to precise time delta between pairs of events. FIG. 15 shows the result of further combinations between pairs of events. These combinations enable an activated network to be constructed from the data.

After finding the activated network for each task in the previous stage, the timing of each event in each network is extracted from the raw ERP's of each subject. The raw activities of all electrodes at those times are then utilized for standard source localization (LORETA, described previously). The voxels activities are summarized over Talairach-defined Brodmann areas, although it should be noted that any other type of functional or neuropsychological area division or categorization could optionally be used. The activity of each region is normalized with z-score so as to overcome inter-subject structural differences which cause different electrode readings between subjects due to different conductivity. The z-scores of activity for each region in each subject are ordered and the rank of at the activity timing is computed. A uniform rank threshold is computed. If sufficient subjects show activity above this threshold, the region is preferably considered significantly active for this network activity. Regardless of the exact cortical region categorization that is used, the output of this stage is a set of cortical regions (for example and without limitation, Brodmann areas) with the greatest likelihood to form a functional network involved in a given task.

Furthermore, it is also possible to use the Talairach Distance to estimate the location of the subset of electrodes that would be expected to provide the most useful information regarding a particular pattern, determined as described above. The coordinates of the N regions in the target network activity pattern are marked by $Ti(x,y,z)$, $i=1, \ldots, N$, and the coordinates of the M regions in the observed network activity pattern are marked by $Oj(x,y,z)$, $j=1, \ldots, M$.

For each $Oj(x,y,z)$, $j=1, \ldots, M$, the distance is computed to the nearest $Ti(x,y,z)$, $i=1, \ldots, N$, and mark it by $Dj$.

The Talairach Distance is then computed by Eq. 1:

$$TD = \frac{\sum_{j=1}^{M} Dj}{M}$$

Based on application of spatio-temporal pattern recognition methods to the EEG electrodes data as described herein, or any other method, one can find a reduced set of electrodes that are sufficient for separating between different normal or abnormal responses to a specific set of stimuli. The electrodes can be directed in the optimal way for the specific task being performed by the subject.

Optionally and preferably, the above localization may be adjusted according to a weighting parameter. This weighting parameter determines the extent to which preference is given to activity near the electrode. Such preference may optionally be made due the possibility that activity in two or more neighboring areas, may actually be occurring underneath the external tissue. If the parameter is given a weight of zero, then the resultant localization is identical to that obtained through LORETA.

Figure 16:
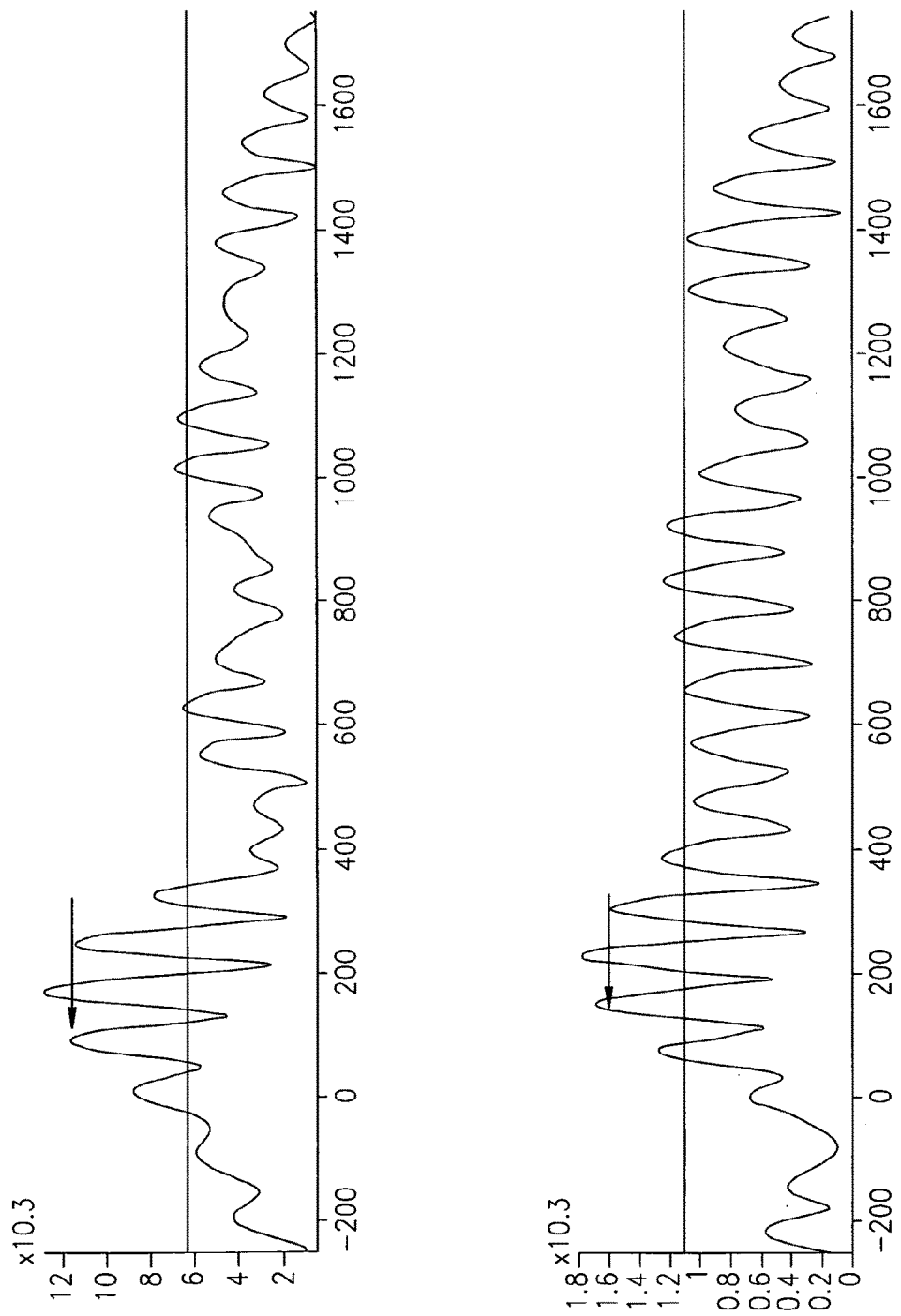
FIG. 16 shows the localized activity of region BA20 right (5-8 Hz) for two subjects after face stimulus.
Figure 17:
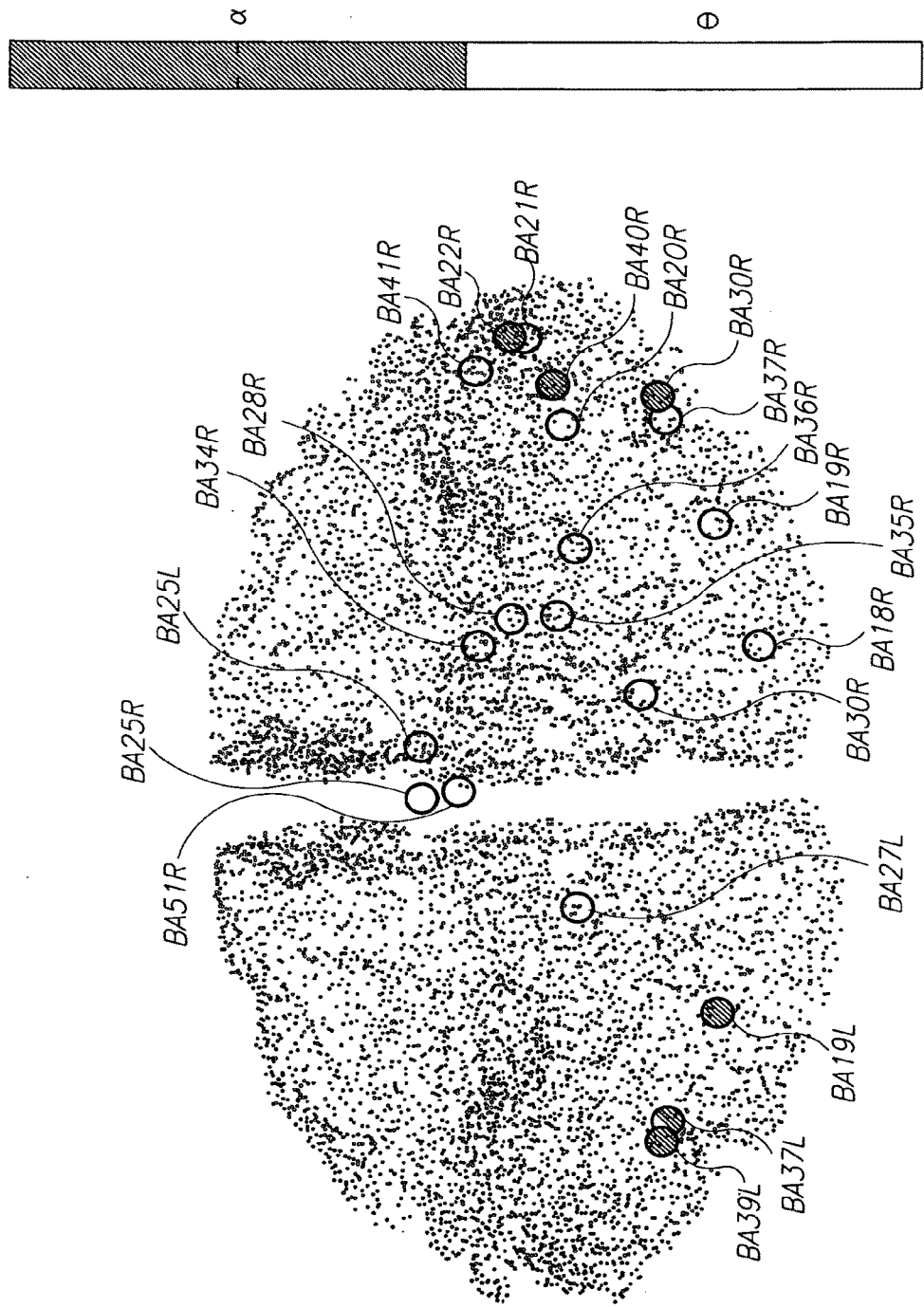
FIG. 17 shows regions of network found significant in 9 subjects at ~N170 timing following face stimulus.

FIG. 16 shows the localized activity of region BA20 right (5-8 Hz) for two subjects after face stimulus. Times of one network activity are marked with arrow as well as threshold of significance (85%) for each subject. The region crosses the threshold 9/9 which is statistically significant. FIG. 17 shows regions of network found significant in 9 subjects at ~N170 timing following face stimulus. The same network did not occur at all after the chair stimulus (ie viewing a chair, which is an inanimate object, as opposed to a face).

The above processes support analysis by single trials. For such an analysis to be performed, first a plurality of single trials is performed on different individuals, preferably a large number of such individuals (for example and without limitation, hundreds, thousands and so forth), rather than performing multiple trials on a single individual (and then repeating for a plurality of individuals). Statistical strength is obtained by performing single trials with multiple individuals, as each such trial is therefore not related to any other trial; also, it is not necessary to compare two groups in order to obtain statistical strength, even though the Z-score is much lower in single trials because of a greater amount of noise. Single trials also provide additional detection sensitivity as averaging may result in loss of the actual signal, as the brain activity or activities may not be identical between trials in a single person. Therefore, single trials may also provide more data than multiple trials performed on a single subject.

Once a pattern has been determined by performing such single trials on multiple individuals, it is possible to analyze a single trial from a single individual according to the pattern of signals obtained from multiple electrodes with specific timing, which is then compared to the previously obtained pattern.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

The invention claimed is:

1. A method of determining a brain activity pattern, the method comprising:
    using an EEG or brain imaging tool for obtaining neurophysiological data from a subject, while or after said subject is performing a task;
    using a data processor communicating with said EEG or brain imaging tool for:
    decomposing the data into a plurality of waveforms;
    identifying within said waveforms three-dimensional data patterns according to latency, amplitude and frequency of peaks of said waveforms; and
    determining brain activity patterns based on said data patterns; and
    displaying a graphic presentation of said activity patterns, said graphic presentation presenting brain regions that are active while or after said subject is performing said task.

2. The method according to claim 1, further comprising decomposing the data into a plurality of peaks.

3. The method according to claim 1, wherein the data are decomposed to a plurality of overlapping sets of waveforms.

4. The method according to claim 1, further comprising comparing said data patterns to a previously determined pattern.

5. The method according to claim 1, further comprising searching through a database of previously determined data patterns and selecting from said database a pattern closest to at least one of said identified data patterns.

6. The method according to claim 1, further comprising obtaining neurophysiological data also from at least one additional subject for a particular behavioral process, and associating said brain activity patterns with said behavioral process.

7. The method according to claim 1, wherein said neurophysiological data comprise data pertaining to a spontaneous brain activity.

8. The method according to claim 1, further comprising clustering said waveforms according to at least one of said latency, said amplitude and said frequency of peaks of said waveforms, to provide a plurality of clusters.

9. The method according to claim 1, further comprising determining a causality relation among data pattern components, and utilizing said relation to determine an activity network among said data patterns.

10. The method according to claim 9, further comprising determining a brain network activity (BNA) correlation to said activity network.

11. The method according to claim 10, wherein said determination of said BNA correlation comprises determining synchronization, or lack thereof, between a plurality of areas of the brain.

12. The method according to claim 10, wherein said identifying said data patterns comprises identifying source localizations for said BNA.

13. The method according to claim 12, further comprising comparing said data patterns to a previously determined pattern and correcting said source localizations based on said comparison.

14. The method according to claim 1, wherein said neurophysiological data comprises EEG signals.

15. The method according to claim 1, wherein said decomposing the data is effected by a wavelet transform.

16. The method according to claim 1, wherein said task is a conceptual task.

* * * * *